United States Patent
Friedman et al.

(10) Patent No.: US 11,179,171 B2
(45) Date of Patent: Nov. 23, 2021

(54) RADIAL EXPANSION CONTROL MECHANISMS FOR INTRALUMINAL DEVICE

(71) Applicant: RAPID MEDICAL LTD., Yokneam (IL)

(72) Inventors: Aharon Friedman, Haifa (IL); Matan Gedulter, Givat Ela (IL); Moshe Miller, Jerusalem (IL)

(73) Assignee: RAPID MEDICAL LTD., Yokneam (IL)

( * ) Notice: Subject to any disclaimer, the term of this patent is extended or adjusted under 35 U.S.C. 154(b) by 86 days.

(21) Appl. No.: 16/265,891

(22) Filed: Feb. 1, 2019

(65) Prior Publication Data

US 2019/0167284 A1    Jun. 6, 2019

Related U.S. Application Data

(63) Continuation-in-part of application No. PCT/IB2017/001773, filed on Dec. 18, 2017.
(Continued)

(51) Int. Cl.
*A61B 17/221* (2006.01)
*A61F 2/01* (2006.01)
(Continued)

(52) U.S. Cl.
CPC .............. *A61B 17/221* (2013.01); *A61F 2/01* (2013.01); *A61B 2017/0042* (2013.01);
(Continued)

(58) Field of Classification Search
CPC .......... A61B 17/221; A61B 2017/2212; A61B 2017/2215; A61F 2002/016
See application file for complete search history.

(56) References Cited

U.S. PATENT DOCUMENTS

| 5,490,859 A | 2/1996 | Mische et al. |
| 2002/0169474 A1 | 11/2002 | Kusleika et al. |

(Continued)

FOREIGN PATENT DOCUMENTS

| CN | 1269707 A | 10/2000 |
| CN | 103841905 A | 6/2014 |

(Continued)

OTHER PUBLICATIONS

International Search Report and Written Opinion of the International Searching Authority dated Jul. 10, 2018, in International Application No. PCT/IB2017/001773 (8 pages).
(Continued)

*Primary Examiner* — Katrina M Stransky
*Assistant Examiner* — Mohammed S Adam
(74) *Attorney, Agent, or Firm* — Finnegan, Henderson, Farabow, Garrett & Dunner, LLP

(57) ABSTRACT

An intraluminal device and a method of removing a clot from a body lumen with an intraluminal device may be provided. The intraluminal device may include a hollow elongated shaft and a radially-expandable mesh segment situated distal to the elongated shaft. The elongated shaft may be secured relative to a first portion of the mesh segment. The intraluminal device may additionally include a core wire affixed to a second portion of the mesh segment and extending through the elongated shaft. The elongated shaft may be configured to radially expand the mesh segment by axially moving the first portion of the mesh segment relative to the second portion of the mesh segment. In addition, the core wire may be configured to radially expand the mesh segment by axially moving the second portion of the mesh segment relative to the first portion of the mesh segment.

8 Claims, 27 Drawing Sheets

Related U.S. Application Data

(60) Provisional application No. 62/435,796, filed on Dec. 18, 2016.

(51) Int. Cl.
*A61B 17/22* (2006.01)
*A61B 17/00* (2006.01)

(52) U.S. Cl.
CPC .............. *A61B 2017/00367* (2013.01); *A61B 2017/22034* (2013.01); *A61B 2017/22072* (2013.01); *A61B 2017/22094* (2013.01); *A61F 2002/016* (2013.01); *A61F 2230/0026* (2013.01); *A61F 2230/0097* (2013.01); *A61F 2250/0023* (2013.01); *A61F 2250/0039* (2013.01)

(56) References Cited

U.S. PATENT DOCUMENTS

| | | |
|---|---|---|
| 2009/0299393 A1 | 12/2009 | Martin et al. |
| 2011/0213403 A1 | 9/2011 | Aboytes |
| 2014/0128905 A1 | 5/2014 | Molaei |
| 2015/0182361 A1 | 7/2015 | Ferrera et al. |
| 2015/0196744 A1 | 7/2015 | Aboytes |
| 2017/0056034 A1 | 3/2017 | Krolik et al. |
| 2017/0354402 A1 | 12/2017 | Lee et al. |

FOREIGN PATENT DOCUMENTS

| | | |
|---|---|---|
| GB | 2020557 A | 11/1979 |
| WO | WO 2009/086482 A1 | 7/2009 |
| WO | WO 2011/106426 A1 | 9/2011 |
| WO | WO 2013/102848 A2 | 7/2013 |
| WO | WO 2016/125018 A2 | 8/2016 |
| WO | WO 2017/077393 A1 | 5/2017 |
| WO | WO 2018/109566 A2 | 6/2018 |

OTHER PUBLICATIONS

Extended European Search Report dated Jun. 8, 2020, by the European Patent Office in European Application No. 17880659.2 (8 pages).

International Search Report and Written Opinion of the International Searching Authority dated Aug. 31, 2020, in International Application No. PCT/IB2020/000223 (12 pages).

First Office Action and Search Report dated Mar. 3, 2021, by the China National Intellectual Property Administration in Chinese Application No. 201780077640.4, with Translation (14 pages).

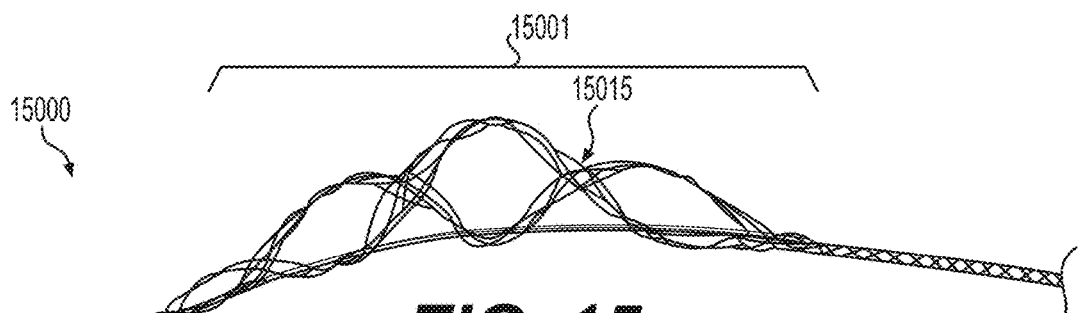
FIG. 15
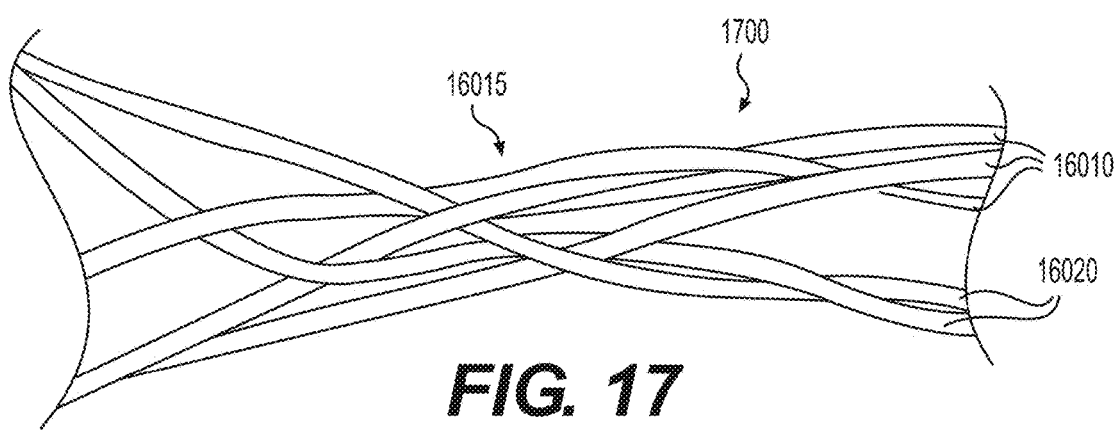
FIG. 16
FIG. 17
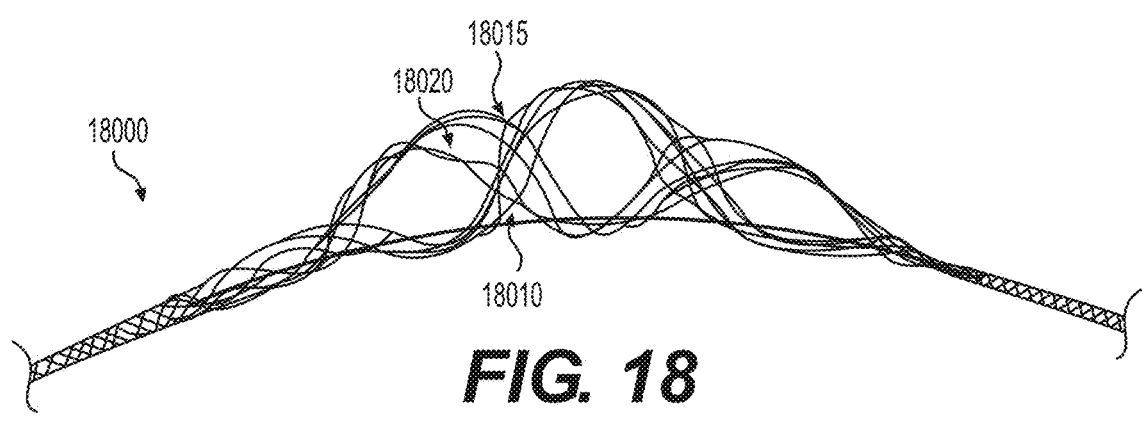
FIG. 18

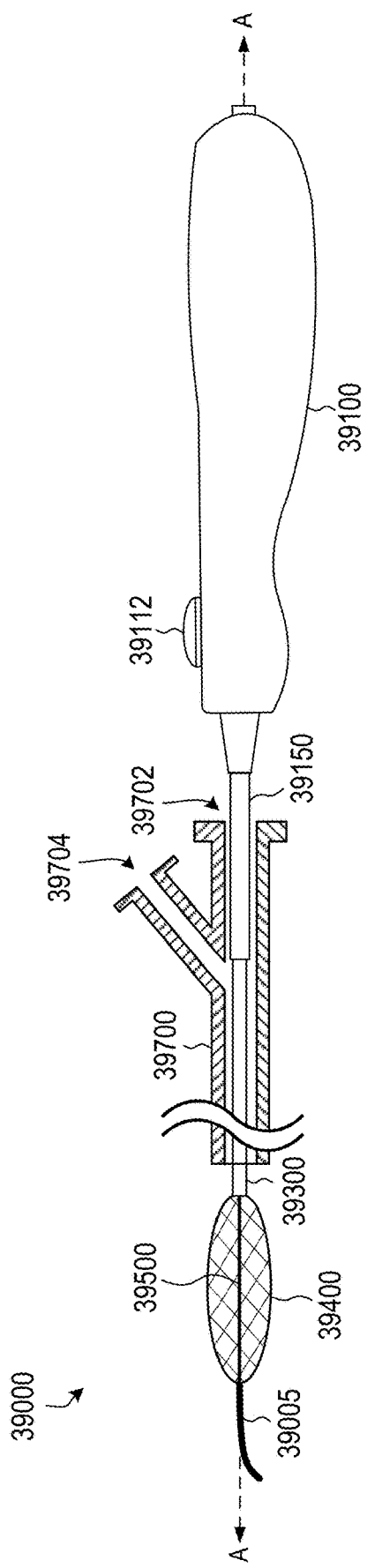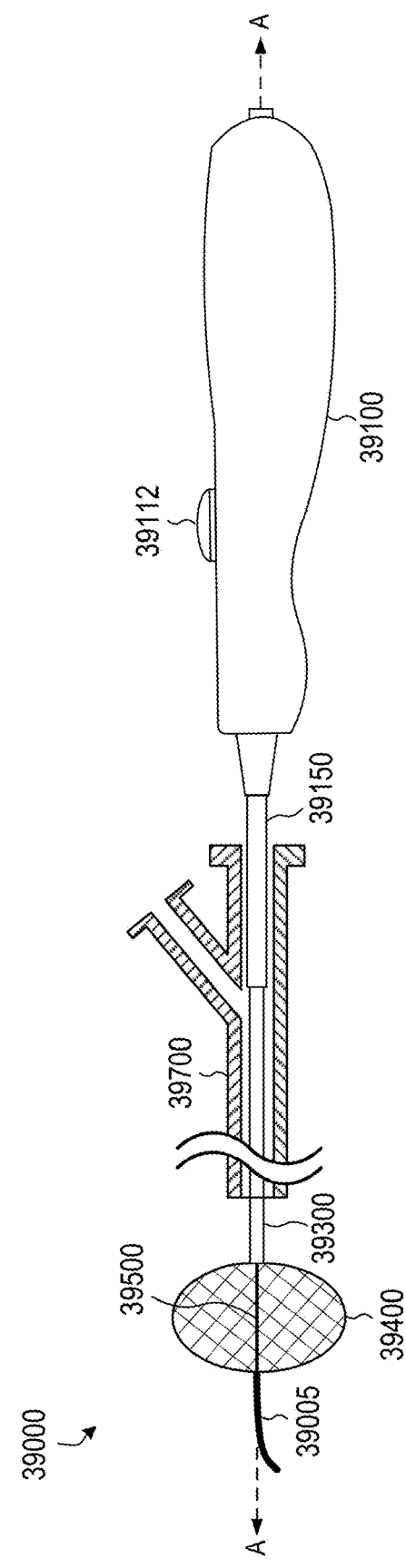

RADIAL EXPANSION CONTROL MECHANISMS FOR INTRALUMINAL DEVICE

CROSS-REFERENCE TO RELATED APPLICATIONS

This application is a Continuation-In-Part of International Application No. PCT/IB2017/001773, filed Dec. 18, 2017, which claims the benefit of priority from U.S. Provisional Application No. 62/435,796, filed Dec. 18, 2016, both of which are herein incorporated by reference in their entireties.

TECHNICAL FIELD

This disclosure relates to intravascular and/or intraluminal medical devices that are configured to retrieve an obstruction from human blood vessels. Obstructions to be retrieved can include clots and clot material.

SUMMARY

Embodiments of the present disclosure may include an intraluminal device including a hollow elongated shaft extending between a distal end thereof and a proximal end thereof. The intraluminal device may additionally include a first mesh segment situated distal to the elongated shaft. The first mesh segment may be configured to transition between a radially-contracted state and a radially-expanded state. In the radially-contracted state, a distal end of the first mesh segment may be spaced a first distance from a proximal end of the first mesh segment. In the radially-expanded state, the distal end of the first mesh segment may be spaced a second distance from the proximal end of the first mesh segment. The first distance may be greater than the second distance. The intraluminal device may additionally include a core wire affixed to at least a portion of the first mesh segment. The core wire may be configured for axial movement. The axial movement of the core wire may control movement of the first mesh segment between the radially-contracted state and the radially-expanded state by adjusting a distance between the proximal and distal ends of the first mesh segment. The intraluminal device may additionally include a first mesh expansion limiter situated at least partially within the first mesh segment. The first mesh expansion limiter may be configured to hold the proximal and distal ends of the first mesh segment apart by a minimum distance equal to the second distance.

The core wire may be affixed to the distal end of the first mesh segment. The proximal end of the first mesh segment may be secured to the distal end of the elongated shaft. The first mesh segment may include a plurality of wires woven to form the first mesh segment. The first mesh segment may be configured to capture a blood clot. The first mesh segment may be configured to be retained within a delivery catheter when the first mesh segment is in the radially-contracted state. The first mesh segment may be configured to assume a first diameter when the first mesh segment is in the radially-contracted state. The first mesh segment may also be configured to assume a second diameter when the first mesh segment is in the radially-expanded state. The second diameter may be larger than the first diameter. The first mesh expansion limiter may be configured to prevent radial expansion of the first mesh segment beyond the second diameter. The first mesh expansion limiter may include a cylindrical shaft having an axial length approximately equal to the second distance. The first mesh expansion limiter may include an elastic coil configured to have a minimum axial length approximately equal to the second distance. The elastic coil may be configured to stretch from an axial length equal to the second distance to an axial length equal to the first distance. The elastic coil of the first mesh expansion limiter may be contained within the first mesh segment and may be configured to abut the proximal and distal ends of the first mesh segment. The elastic coil of the first mesh expansion limiter may be biased to hold the proximal and distal ends of the first mesh segment apart by at least the first distance. The intraluminal device may additionally include a second mesh segment arranged between the first mesh segment and the distal end of the elongated shaft. The second mesh segment may be configured to transition between a radially-contracted state and a radially-expanded state. In the radially-contracted state, a distal end of the second mesh segment may be spaced a third distance from a proximal end of the second mesh segment. In the radially-expanded state, the distal end of the second mesh segment may be spaced a fourth distance from the proximal end of the second mesh segment. The third distance may be greater than the fourth distance. The axial movement of the core wire may control movement of the second mesh segment between the radially-contracted state and the radially-expanded state by adjusting a distance between the proximal and distal ends of the second mesh segment. The intraluminal device may additionally include a second mesh expansion limiter situated at least partially within the second mesh segment. The second mesh expansion limiter may be configured to hold the proximal and distal ends of the second mesh segment apart by a minimum distance equal to the fourth distance. The second mesh expansion limiter may include a cylindrical shaft having an axial length approximately equal to the fourth distance. The second mesh expansion limiter may include an elastic coil configured to have a minimum axial length approximately equal to the fourth distance and configured to extend from the fourth distance to the third distance. The elastic coil of the second mesh expansion limiter may be contained within the second mesh segment and may be configured to abut the proximal and distal ends of the second mesh segment. The elastic coil of the second mesh expansion limiter may be biased to hold the proximal and distal ends of the second mesh segment apart by at least the third distance. The first mesh segment may be configured for radial expansion independent of radial expansion of the second mesh segment. The core wire may be devoid of connections to the second mesh segment.

Alternative embodiments of the present disclosure may include a method of removing occlusive material from a body lumen. The method may include positioning a first mesh segment of an intraluminal device downstream of the occlusive material in the body lumen. The first mesh segment may be arranged in a first radially-contracted state in which a distal end of the first mesh segment may be spaced a first distance from a proximal end of the first mesh segment. The method may additionally include arranging the first mesh segment in a first radially-expanded state in which the distal end of the first mesh segment may be spaced a second distance from the proximal end of the first mesh segment. The first distance may be greater than the second distance. A first mesh expansion limiter situated at least partially within the first mesh segment may prevent a distance between the proximal and distal ends of the first mesh segment from decreasing below the second distance. The method may additionally include moving the radially-expanded first mesh segment into engagement with the occlusive material. The method may additionally include removing the occlusive material by moving the radially-expanded first mesh segment in an upstream direction.

The intraluminal device may include a hollow elongated shaft having a distal end and a proximal end. The first mesh segment may be situated distally of the elongated shaft. The intraluminal device may additionally include a core wire affixed to at least a portion of the first mesh segment. Axial movement of the core wire may control movement of the first mesh segment between the first radially-contracted state and the first radially-expanded state by adjusting a distance between the proximal and distal ends of the first mesh segment. The core wire may be affixed to the distal end of the first mesh segment and the proximal end of the first mesh segment may be secured to the distal end of the elongated shaft. The first mesh expansion limiter may prevent radial expansion of the first mesh segment beyond a predetermined diameter while the first mesh segment is arranged in the first radially-expanded state. The first mesh expansion limiter may include a cylindrical shaft having an axial length approximately equal to the second distance. The first mesh expansion limiter may include an elastic coil. The elastic coil may have a first axial length approximately equal to the first distance during positioning of the first mesh segment downstream of the occlusive material and a second axial length approximately equal to the second distance while the first mesh segment is arranged in the first radially-expanded state. The elastic coil of the first mesh expansion limiter may be contained within the first mesh segment and may abut the proximal and distal ends of the first mesh segment during positioning of the first mesh segment downstream of the occlusive material. The method may additionally include positioning a second mesh segment of the intraluminal device in the body lumen while the second mesh segment is arranged in a second radially-contracted state in which a distal end of the second mesh segment may be spaced a third distance from a proximal end of the second mesh segment. The method may additionally include arranging the second mesh segment in a second radially-expanded state in which the distal end of the second mesh segment may be spaced a fourth distance from the proximal end of the second mesh segment. The third distance may be greater than the fourth distance. A second mesh expansion limiter situated at least partially within the second mesh segment may prevent a distance between the proximal and distal ends of the second mesh segment from decreasing below the fourth distance. The second mesh segment may be arranged in the second radially-expanded state prior to the first mesh segment being arranged in the first radially-expanded state. The second mesh segment may be arranged in the second radially-expanded state after the first mesh segment is arranged in the first radially-expanded state. The second mesh expansion limiter may prevent radial expansion of the second mesh segment beyond a predetermined diameter while the second mesh segment is arranged in the second radially-expanded state. The second mesh expansion limiter may include a cylindrical shaft having an axial length approximately equal to the fourth distance. The second mesh expansion limiter may include an elastic coil. The elastic coil may have a first axial length approximately equal to the third distance during positioning of the second mesh segment in the body lumen and a second axial length approximately equal to the fourth distance while the second mesh segment is arranged in the second radially-expanded state. The elastic coil of the second mesh expansion limiter may be contained within the second mesh segment and may abut the proximal and distal ends of the second mesh segment during positioning of the second mesh segment in the body lumen.

Further alternative embodiments of the present disclosure may include an intraluminal device having a hollow elongated shaft that may include a distal end and a proximal end. The intraluminal device may additionally include a first radially-expandable mesh segment situated distal to the elongated shaft. The elongated shaft may be secured relative to a first portion of the first mesh segment. The intraluminal device may additionally include a core wire affixed to a second portion of the first mesh segment and extending through the elongated shaft. The elongated shaft may be configured to radially expand the first mesh segment by axially moving the first portion of the first mesh segment relative to the second portion of the first mesh segment. The core wire may be configured to radially expand the first mesh segment by axially moving the second portion of the first mesh segment relative to the first portion of the first mesh segment.

The first portion of the first mesh segment may include a proximal end of the first mesh segment. The second portion of the first mesh segment may include a distal end of the first mesh segment. The axial movement of the first portion of the first mesh segment may be in a distal axial direction relative to the second portion of the first mesh segment. The axial movement of the second portion of the first mesh segment may be in a proximal axial direction relative to the first portion of the first mesh segment. The elongated shaft and core wire may be configured to simultaneously radially expand the first mesh segment. The elongated shaft and core wire may be configured to effect equidistant axial movement of the first portion of the first mesh segment and the second portion of the first mesh segment, respectively. The intraluminal device may additionally include a handle situated proximal to the elongated shaft. The elongated shaft and the core wire may be configured for axial movement relative to the handle. The handle may include a first handle segment secured relative to the core wire and a second handle segment secured relative to the elongated shaft. The first handle segment and second handle segment may be configured for equidistant movement in opposite axial directions. The handle may be configured to be secured relative to a delivery catheter such that the elongated shaft and the core wire may be configured for axial movement relative to the delivery catheter. The handle may additionally include a locking shaft extending from the distal end of the handle over at least a portion of the elongated shaft. The locking shaft of the handle may be configured to be secured to at least a portion of the delivery catheter. The first mesh segment may include a plurality of wires woven to form the first mesh segment. The first mesh segment may be configured to capture a blood clot. The intraluminal device may additionally include a second radially-expandable mesh segment situated between the first mesh segment and the elongated shaft. The elongated shaft may be affixed to a proximal end of the second mesh segment and may be configured to radially expand the first mesh segment and the second mesh segment by axially moving the proximal end of the second mesh segment. The core wire may be configured to radially expand the first mesh segment and the second mesh segment by axially moving a distal end of the first mesh segment. The second mesh segment may include a plurality of wires woven to form the second mesh segment. The second mesh segment may be configured to capture a blood clot.

A still further embodiment of the present disclosure may include a method of removing a clot from a body lumen. The method may include positioning a radially-expandable mesh segment of an intraluminal device downstream of the clot in the body lumen while the mesh segment is in a radially-contracted state. The mesh segment may include a proximal end and a distal end. The method may additionally include radially-expanding the mesh segment by moving the proximal end of the mesh segment a first distance in a first direction and by moving the distal end of the mesh segment a second distance in a second direction. The first distance may be equal to the second distance. The first direction may be opposite the second direction. The method may additionally include moving the radially-expanded mesh segment into engagement with the clot. The method may additionally include removing the clot by moving the radially-expanded mesh segment in an upstream direction.

The proximal and distal ends of the mesh segment may move simultaneously during radial expansion of the mesh segment. The first direction may be a distal direction and the second direction may be a proximal direction. The intraluminal device may include a hollow elongated shaft situated proximal to the mesh segment. The elongated shaft may be secured relative to the proximal end of the mesh segment. The intraluminal device may additionally include a core wire affixed to the distal end of the mesh segment. The intraluminal device may additionally include a handle situated proximal to the elongated shaft. The elongated shaft and the core wire may move axially relative to the handle during radial expansion of the mesh segment. The elongated shaft and the core wire may move simultaneously to radially expand the mesh segment. Radially-expanding the mesh segment may include axially moving the proximal end of the mesh segment relative to the distal end of the mesh segment with the elongated shaft and axially moving the distal end of the mesh segment relative to the proximal end of the mesh segment with the core wire. The handle may include a first handle segment secured relative to the core wire and a second handle segment secured relative to the elongated shaft. The first handle segment and second handle segment may move the same distance in opposite axial directions during radial expansion of the mesh segment.

BRIEF DESCRIPTION OF THE DRAWINGS

The accompanying drawings, which are incorporated in and constitute a part of this specification, illustrate disclosed embodiments and, together with the description, serve to explain the disclosed embodiments.

FIG. 15 is an illustration of an exemplary intraluminal device, consistent with at least one of the disclosed embodiments;

FIG. 16 is an enlarged view of a portion of the exemplary intraluminal device shown in FIG. 15;

FIG. 17 is an enlarged view of a portion of the exemplary intraluminal device shown in FIG. 15 in an expanded position;

FIG. 18 is an illustration of exemplary intraluminal device in an expanded position, in accordance with at least one of the disclosed embodiments;

FIGS. 39A and 39B illustrate an exemplary intraluminal device delivered through an exemplary catheter, in accordance with at least one of the disclosed embodiments.

Annotations appearing in the figures are exemplary only, and are not restrictive of the invention as claimed.

DETAILED DESCRIPTION

Reference will now be made in detail to the present embodiments (exemplary embodiments) of the disclosure, examples of which are illustrated in the accompanying drawings. Wherever possible, the same reference numbers will be used throughout the drawings to refer to the same or like parts.

Figure 1:
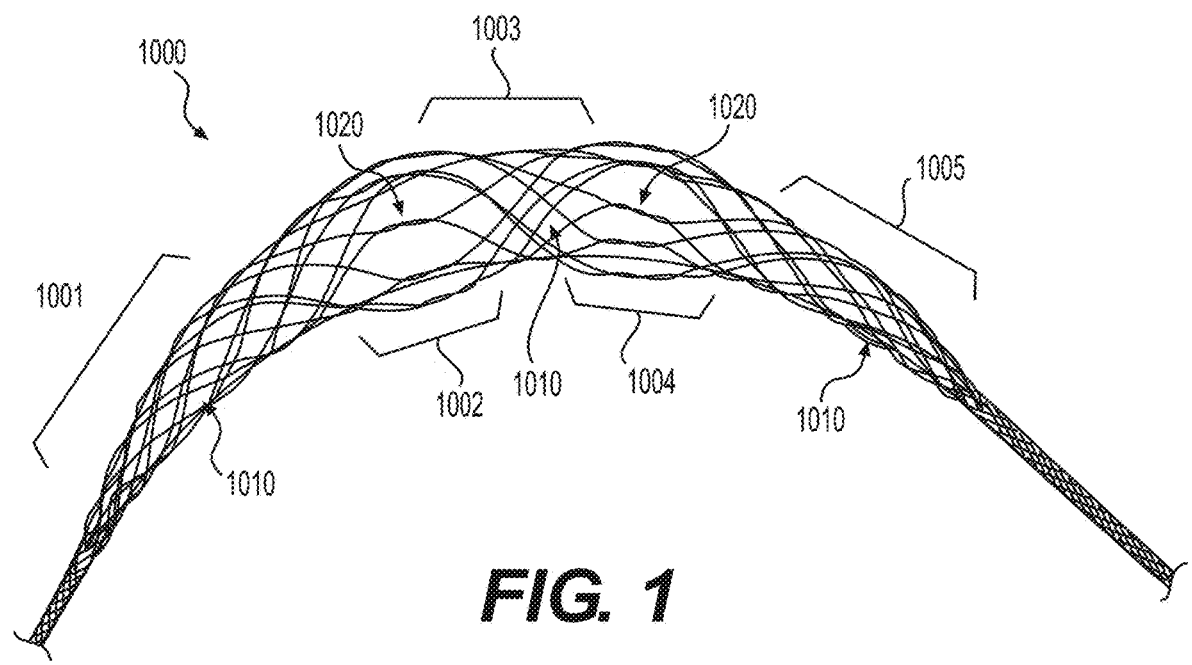
FIG. 1 is an illustration of a first exemplary intraluminal device, consistent with at least one of the disclosed embodiments.
Figure 10B:
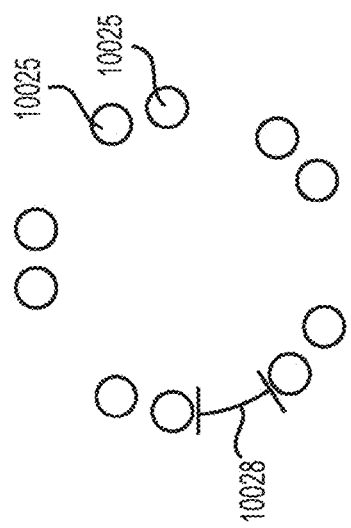
FIG. 10B is a cross-sectional view of a portion of the exemplary intraluminal device shown in FIG. 10A.
Figure 10A:
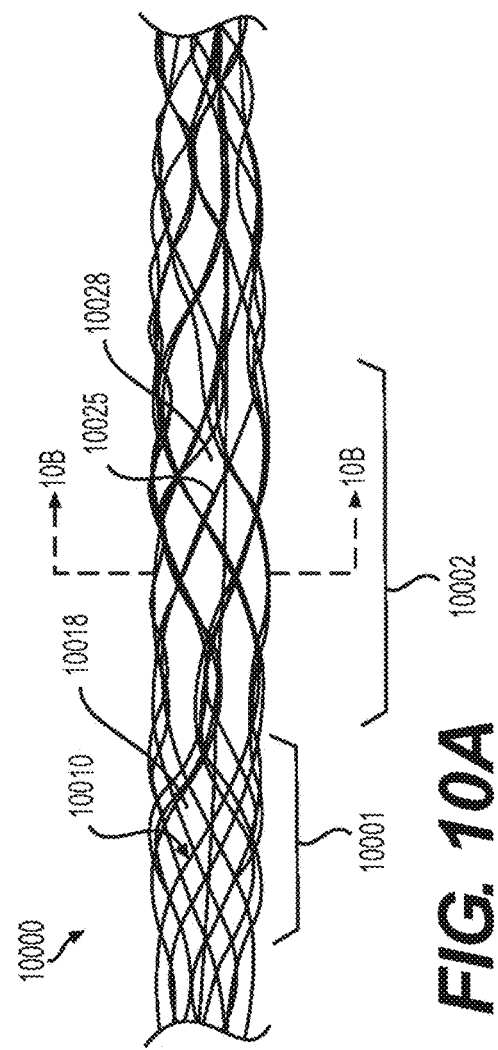
FIG. 10A is an illustration of another exemplary intraluminal device, in accordance with at least one of the disclosed embodiments.

FIG. 1 illustrates an exemplary intraluminal device 1000 including five alternating wire zones 1001, 1002, 1003, 1004, and 1005. Zones 1001, 1003 and 1005 include groups of woven wires 1010 and may provide structural support for zones 1002 and 1004. Additionally, since the openings between wires 1010 of zone 1 and 5 may be much smaller they also may provide a distal and proximal filter. (An example of variable sized openings is illustrated in FIGS. 10A-B, discussed below.) As a result, clot particles that might appear during the retrieval may be captured at these zones, for example. As further shown in FIG. 1, zones 1002 and 1004 may be constructed of looped wires 1020 to allow a large clot capturing area. And also shown in FIG. 1, zones 1001, 1003, and 1005 may be constructed by woven wires 1010. The number of zones illustrated are exemplary. More or less zones may be provided.

Figure 2:
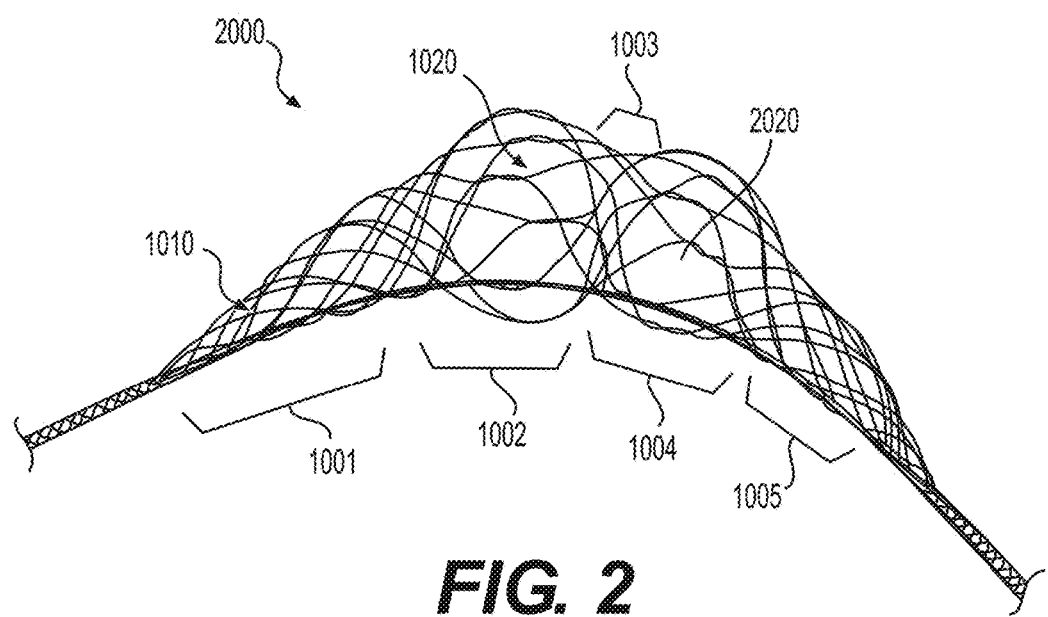
FIG. 2 is an illustration of a second exemplary intraluminal device, in accordance with at least one of the disclosed embodiments.

FIG. 2 illustrates an intraluminal device 2000 in a more open position than illustrated in FIG. 1, highlighting the clot entry cells 2020 that may be made from the looped wires 1020. As further shown in FIG. 2, zones 1002 and 1004 may be constructed of looped wires 1020 to allow a large clot capturing area.

Figure 3:
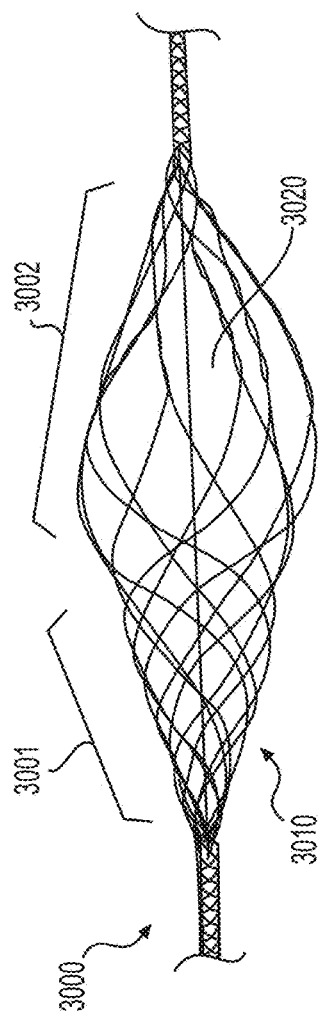
FIG. 3 is an illustration of a third exemplary intraluminal device, in accordance with at least one of the disclosed embodiments.

FIG. 3 illustrates yet another exemplary intraluminal device 3000. In this example, as shown in FIG. 3, the device 3000 may be configured so as to include only two different zones. Zone 3001 may be constructed from a group of woven wires 3010, such as for example, densely braided, which provides structural support for the device 3000. In addition, zone 3001 may also serve as a distal filter that prevents emboli from the distal vasculature. As also shown in FIG. 3, zone 3002 may be constructed from wires which are looped which are longitudinally located and provide the clot entry zone 3020. Additionally, zone 3001 may, for example, give structural support and may also serve as a distal filter. As further shown in FIG. 3, zone 3002 may be the clot entering zone.

Figure 4:
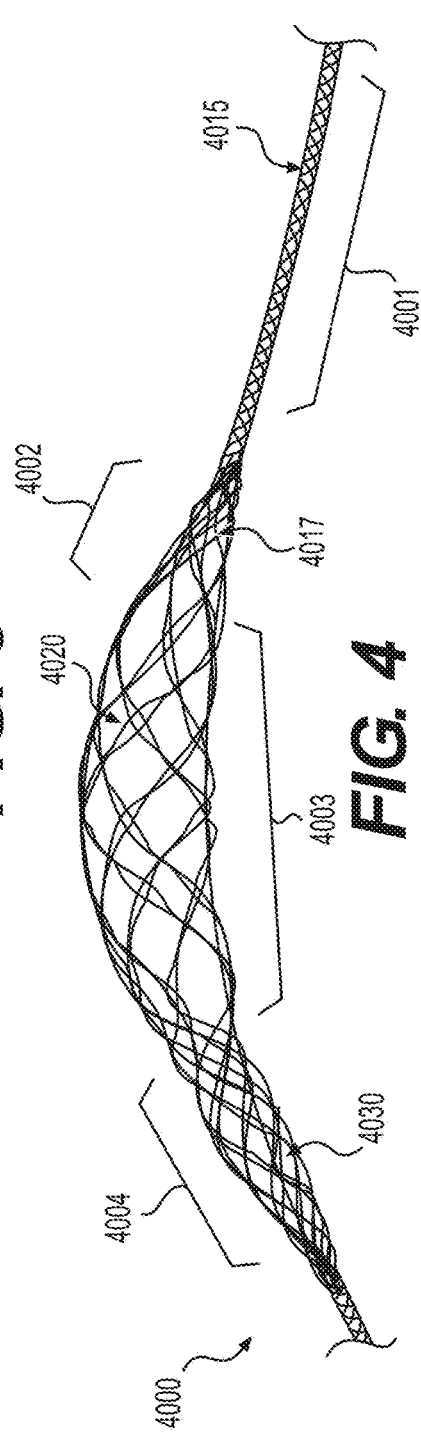
FIG. 4 is an illustration of a fourth exemplary intraluminal device, in accordance with at least one of the disclosed embodiments.

FIG. 4 illustrates yet another exemplary intraluminal device 4000 with four regions. In the first region 4001, the wires may be twisted or coiled to form a shaft 4015. In the second region 4002, the wires may be woven to from a scaffold 4017 that supports the opening of the third region 4003. In the third region 4003, the wires may be woven set in looped pairs to form a clot capture structure 4020. For example, the wires of the third region 4003 may be loosely looped or loosely coupled. Further, the fourth region 4004 may be woven to form a distal filter 4030 that captures distal emboli or clot particles. The fourth region 4004 may also serve as a scaffold for the third region 4003.

Figure 5:
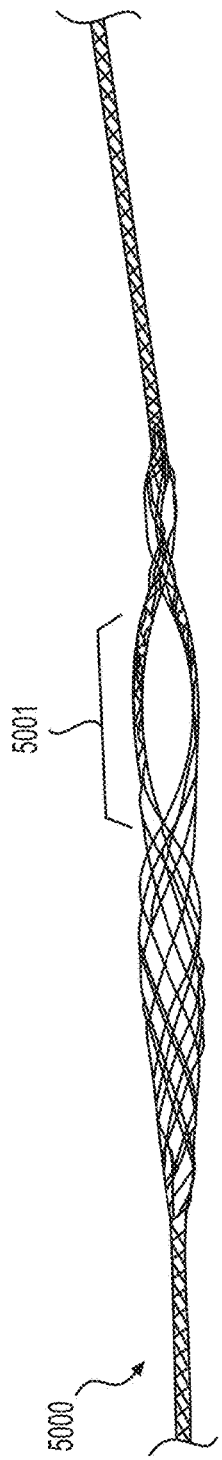
FIG. 5 is an illustration of a fifth exemplary intraluminal device, in accordance with at least one of the disclosed embodiments.

FIG. 5 illustrates yet another exemplary intraluminal device 5000. For example, as shown in FIG. 5, the clot opening region 5001 may be woven from three wires that are looped together. Further, the number of wires that are looped together may be greater than two.

Figure 6:
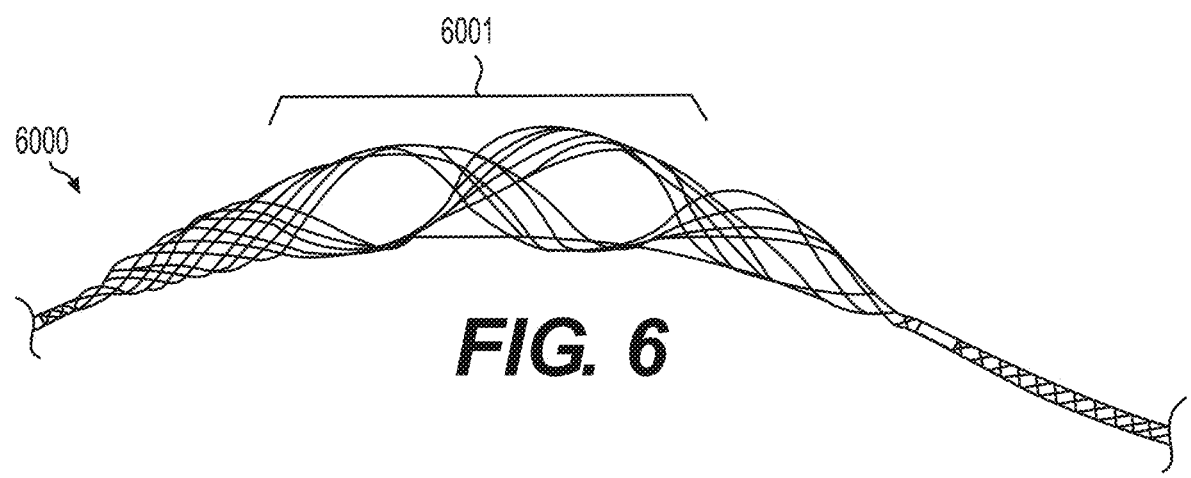
FIG. 6 is an illustration of a sixth exemplary intraluminal device, in accordance with at least one of the disclosed embodiments.

FIG. 6 is illustrates yet another exemplary intraluminal device 6000. For example, as shown in FIG. 6, the clot opening region 6001 may be woven from three wires that are loosely looped together. Further, the number of wires that are looped together may be greater than two.

Figure 7:
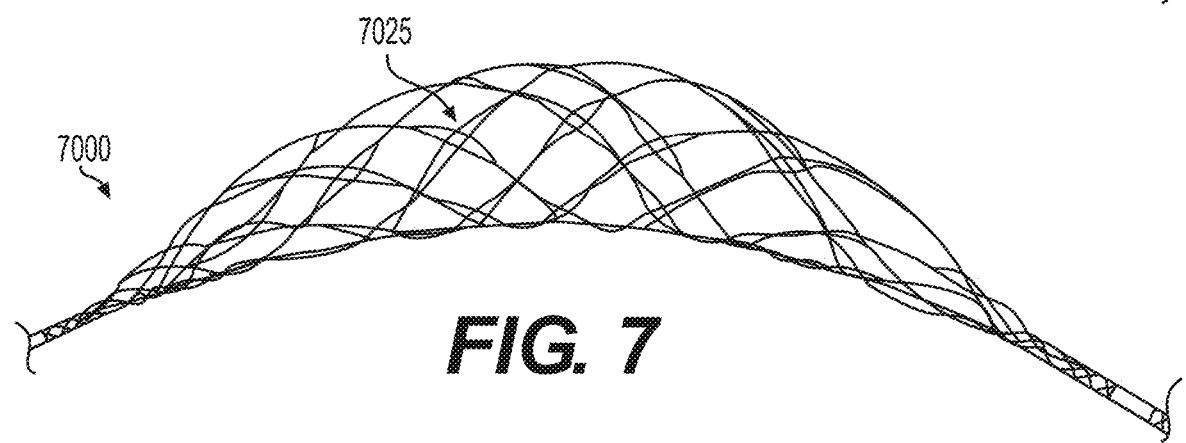
FIG. 7 is an illustration of a seventh exemplary intraluminal device, in accordance with at least one of the disclosed embodiments.

FIG. 7 illustrates yet another exemplary intraluminal device 7000. For example, as shown in FIG. 7, the device 7000 may include six cables 7025, in which each cable 7025 may include paired wires. This may create a strong but flexible crossing. And this may further allow, for example, the device 7000 to achieve a flexible structure with a high radial force.

Figure 8:
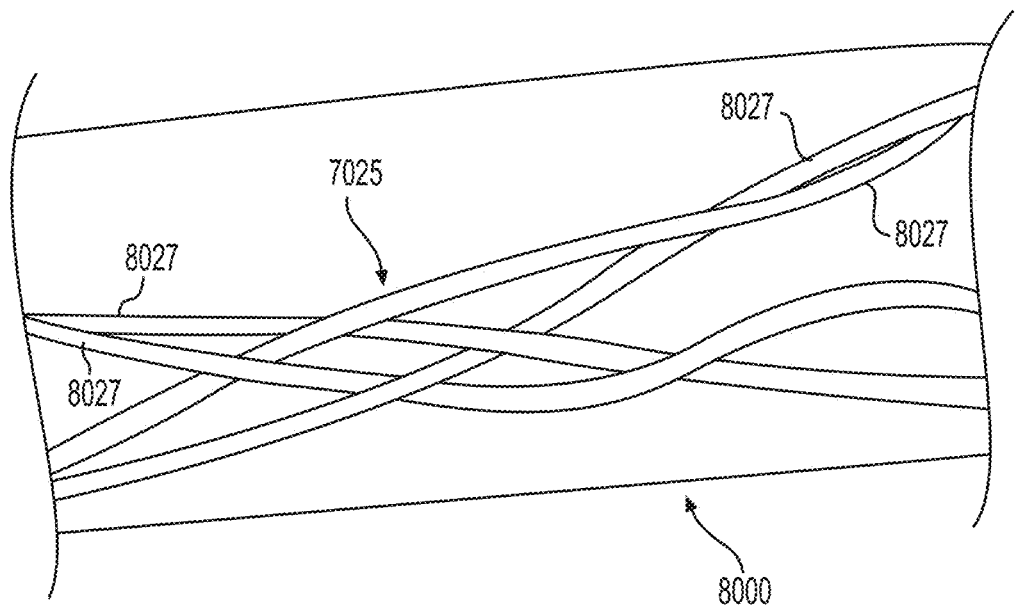
FIG. 8 is an illustration of exemplary cable interweaving, such as is disclosed in connection with FIG. 7.

FIG. 8 illustrates an example of cable interweaving 8000, as discussed above. Each cable 7025, for example, may be made from a looped pair of wires 8027 that are woven with a pair of wires 8027 from a crossing cable. As a result, for example, a semi-flexible and strong crossing point may be achieved.

Figure 9B:
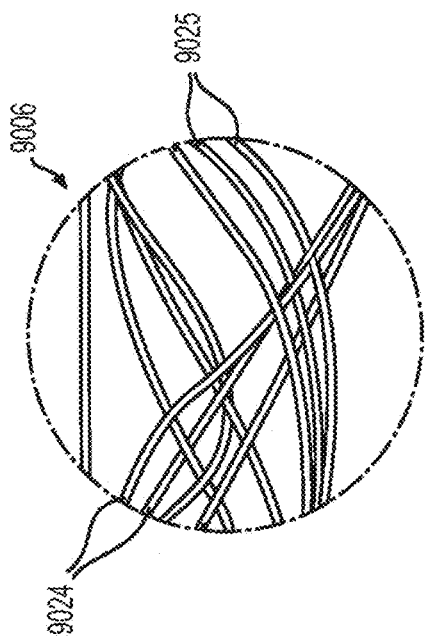
FIG. 9B is an enlarged view of a portion of the exemplary intraluminal device shown in FIG. 9A.
Figure 9A:
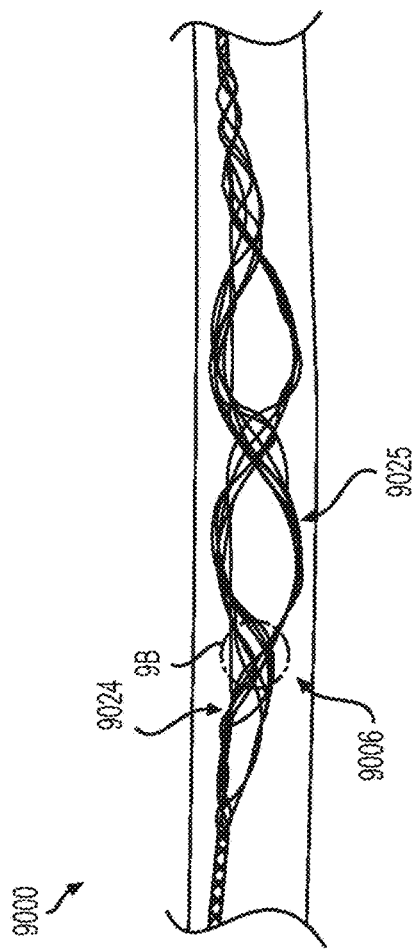
FIG. 9A is an illustration of another exemplary intraluminal device, in accordance with at least one of the disclosed embodiments.

FIGS. 9A-9B illustrate yet another exemplary intraluminal device. As shown in FIG. 9A, the cables, for example, may be made from three wires that are unwound and then woven together with the wires from the crossing cable. FIG. 9B also illustrates the cable crossing point 9006 where the cables (which includes wires 9024 and 9025) are unwound and woven back together. As discussed below in connection with FIGS. 12 and 19, the braiding structure of FIG. 9A may include a 12-wire braiding structure with a twist before and after each junction frame.

As discussed above in connection with FIG. 1, FIG. 10A illustrates device 10000 with variable-sized openings. Region 10001 includes groups of woven wires 10010 adjacent to intermediate location 10002, and may provide structural support for intermediate location 10002. Specifically, the groupings of woven wires 10010 in region 10001 can provide the support to hold open the first interstices 10028. The first interstices 10028 are larger than the second interstices 10018, where the second interstices are present in region 10001. The cross section illustrated in FIG. 10B depicts how the cables 10025 are circumferentially displaced in the intermediate location 10002. Cables 10025 are generally circumferentially displaced about a central region. Moreover, first interstices 10028 may provide relatively large openings for clot entry in the intermediate location 10002.

In accordance with embodiments consistent with the present disclosure, the exemplary intraluminal device may include, for example, two braiding mechanisms, configurations, or structures which may help increase the performance of the device relative to a device incorporating standard braiding structures.

Figure 12:
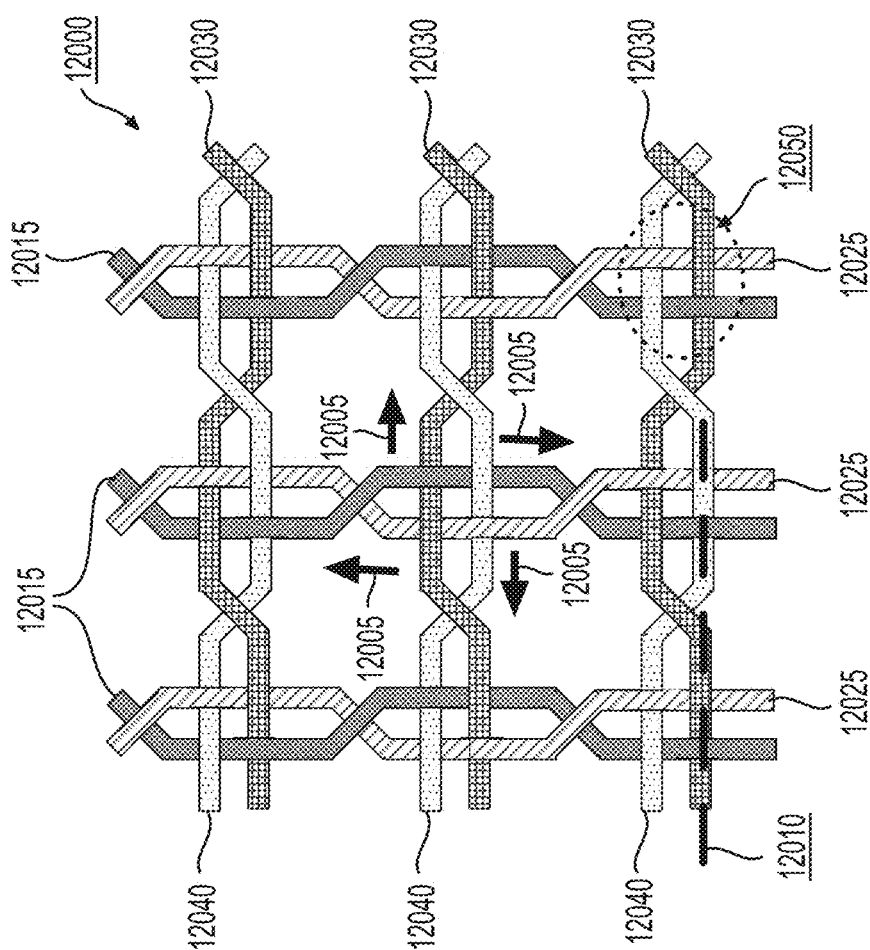
FIG. 12 is an illustration of a braid structure of an exemplary intraluminal device, in accordance with at least one of the disclosed embodiments.
Figure 11:
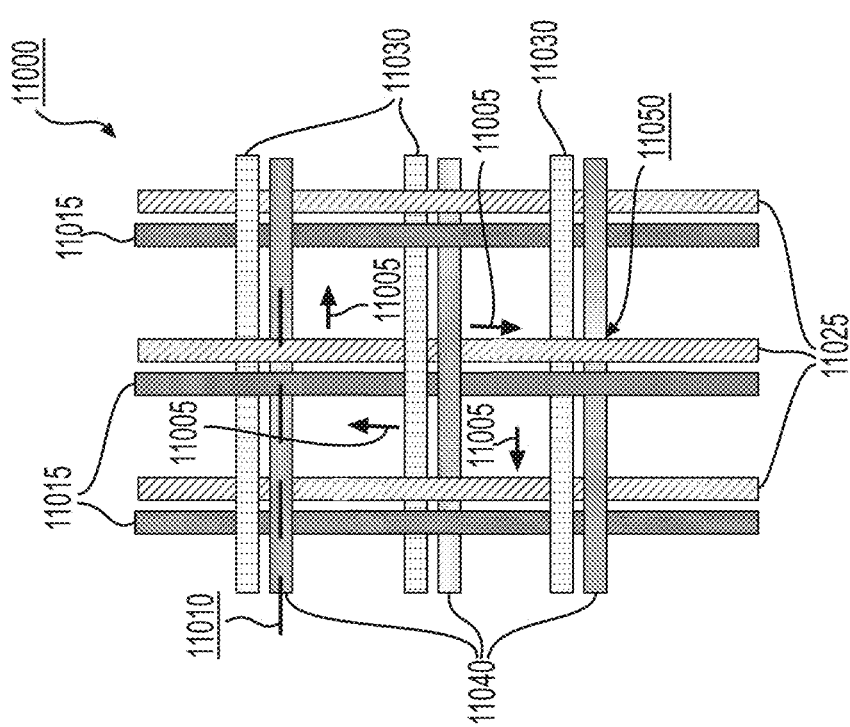
FIG. 11 is an illustration of a braid structure of an exemplary intraluminal device.

For example, as shown in FIG. 12, in accordance with at least some embodiments of an intraluminal device consistent with the present disclosure, the braiding structure 12000 may include a twist of wires before and after each junction frame 12050. Braiding structure 12000 includes three strands of two-wire pairs (two wires 12015 and 12025) braided with three stands of two-wire pairs (two wires 12030 and 12040). FIG. 12 depicts a total of nine (9) junction frames. The junction position within the mesh structure may help prevent slipping of wires across the twist which may otherwise work to become homogeneously separated on a circumference of a mesh structure of an intraluminal device. While a braid structure 11000, as shown in FIG. 11, may enable slippage (illustrated by arrows 11005) until the wire 11040 (for example) reaches a parallel wire 11030, the twists as shown in braiding structure 12000 shown in FIG. 12, may operate to help prohibit substantial slippage across the twist and enable a solid structure when the intraluminal device is expanded.

Figure 13:
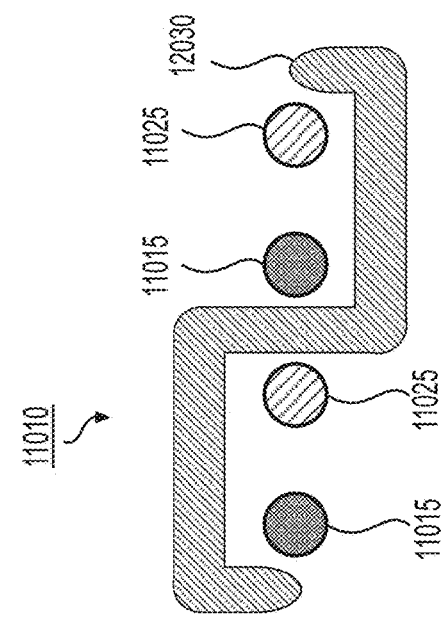
FIG. 13 is a cross section view of an exemplary braided structure without twists, and an associated loaded beam diagram.
Figure 14:
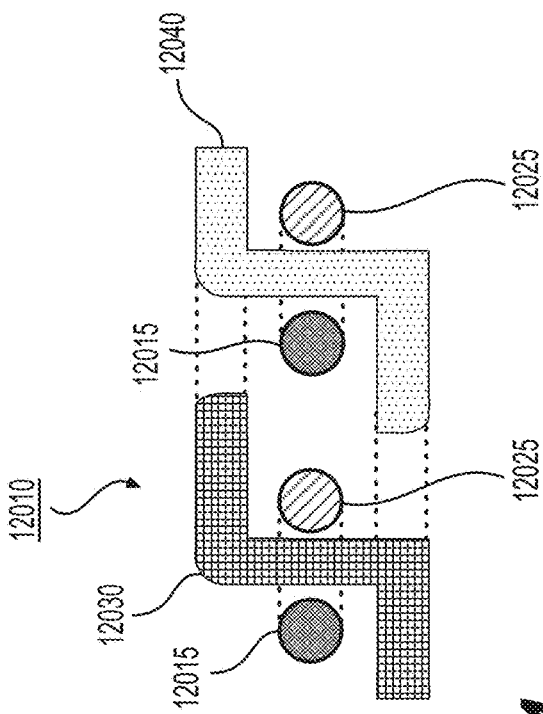
FIG. 14 is a cross section view of an exemplary braided structure with twists, and an associated loaded beam diagram.
Figure 14:
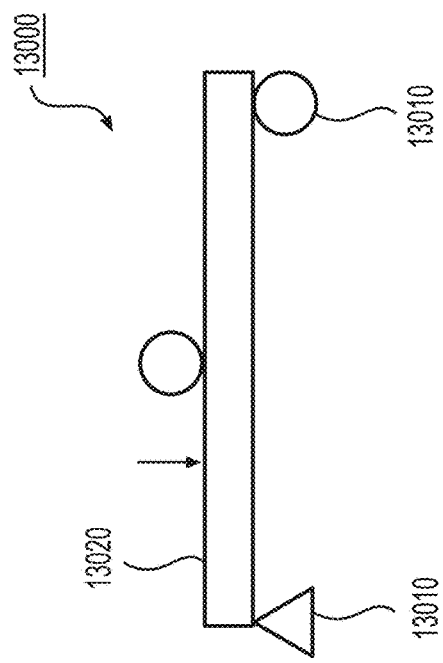
Figure 14:
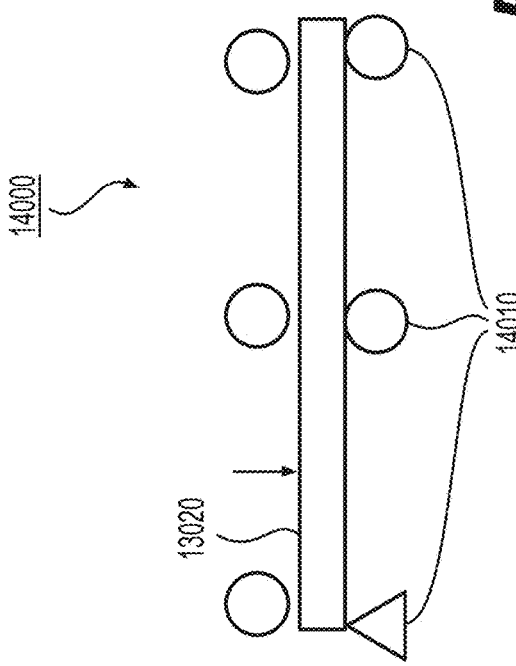

In accordance with at least some embodiments of an intraluminal device consistent with the present disclosure, and as illustrated in FIGS. 13 and 14, a braiding structure which includes a twist structure may add strength to a mesh structure by operating as a restraint system grasping the wire and dividing an external force applied on the mesh onto additional elements. FIG. 13 depicts cross section 11010 of braiding structure 11000 of FIG. 11 and FIG. 14 depicts cross section 12010 of braiding structure 12000 of FIG. 12. The dotted lines in cross section 12010 of FIG. 14 illustrate a twist in wires 12015 and 12025, and also illustrate a twist in wires 12030 and 12040. The force distribution mechanism in the braiding structures is similar, for example, to force distribution of a loaded beam with varying numbers of supports. This is also illustrated in FIGS. 13 and 14 with the loaded beam diagram 13000 (associated with braided structure 11000) and loaded beam diagram 14000 (associated with braided structure 12000). As illustrated in FIGS. 13 and 14, a loaded beam 13020 with three supports 14010, for example, will react to and distribute the force more effectively than a loaded beam 13020 with two supports 13010, as there is a smaller distance between three supports 14010.

In accordance with at least some embodiments consistent with the present disclosure, the exemplary intraluminal device may be delivered through a microcatheter with an internal diameter of between 0.013 inches and 0.027 inches. In some embodiments, the microcatheter may have an internal diameter of 0.017 inches. As a result, the exemplary intraluminal device may have a low profile (in a retracted or compressed state) that is less than that of the internal diameter of a microcatheter. In accordance with at least some embodiments of an intraluminal device consistent with the present disclosure, the device may have the five following parts, for example:

a) a control handle;
    b) a stiff proximal shaft (for example, a stainless steel hypotube);
    c) a flexible shaft (made from a cable of wires, for example);
    d) an expandable mesh which is made from the same wires of the cable; and
    e) a corewire/control wire which may be connected to the distal tip of the mesh and runs through the shafts to the handle.

Figure 19A:
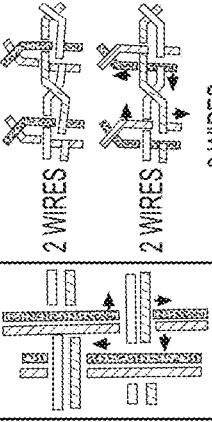
FIGS. 19A-C illustrate a number of braiding structures consistent with at least some of the disclosed embodiments.

For example, as illustrated in the 8-wire row in FIG. 19A, an intraluminal device may include a flexible shaft with eight (8) wires (each wire having a diameter of 70 μm) and a mesh including eight (8) wires (each wire having a diameter of 70 μm). The eight wires, for example, may be formed, for example, by creating four strands of wires braided together, with each strand including two (2) wires each. As shown in FIG. 19A, and discussed above, the braiding structure of the intraluminal device may include a twist of wires before and after each junction frame to help prevent slippage. A detailed view of cable interweaving 8000 (discussed in connection with FIG. 8) is also shown in FIG. 19A. Cable interweaving 8000 illustrates a junction in the braiding structure of the intraluminal device in detail. The wires may, for example, be made from Nitinol. FIG. 19A also depicts a braiding structure of the intraluminal device without a twist before and after a junction frame.

In another exemplary embodiment, as illustrated in the 12-wire row in FIG. 19A, the intraluminal device may include a flexible shaft with twelve (12) wires and a mesh including twelve (12) wires. FIG. 19C depicts a detailed view of the 12-wire row in FIG. 19A. The twelve (12) wires may be formed, for example, by creating six strands of wires braided together: with three strands including two (2) wires each; while the other three strands may include two (2) wires each. As shown in FIG. 19C, and as discussed above (such as in connection with FIG. 8, which shows cable interweaving 8000, and FIG. 12, which shows braiding structure 12000), the braiding structure 12000 for this embodiment may include a twist of wires before and after each junction frame to help prevent slippage. FIG. 19C also depicts braiding structure 11000 without a twist before and after a junction frame. An exemplary intraluminal device with twelve (12) wires includes device 9000 of FIG. 9A.

In accordance with another embodiment consistent with the present disclosure, as illustrated in the 10-wire row in FIG. 19, the flexible shaft of the exemplary intraluminal device may include a flexible shaft with ten (10) wires and a mesh including ten (10) wires. FIG. 19B depicts a detailed view of the 10-wire row in FIG. 19A. The ten (10) wires may be formed, for example, by creating four strands of wires braided together: with two strands including three (3) wires each; while the other two strands may include two (2) wires each. Exemplary braiding structures with ten (10) wires are illustrated in FIG. 19B. The braiding structure 19500 may include a twist of wires before and after each junction frame. Braiding structure 19500 includes two-wire strand (wires 12015 and 12025) and three-wire strand (wires 12015, 12025, and 19025) braided with two-wire strand (wires 12030 and 12040) and three-wire strand (12030, 12040, and 19040). Slippage arrows 19505 are also shown. A braiding structure 19400 without a twist is also illustrated. Braiding structure 19400 includes two-wire strand (wires 11015 and 11025) and three-wire strand (wires 11015, 11025, and 19015) braided with two-wire strand (wires 11030 and 11040) and three-wire strand (11030, 11040, and 19030). Slippage arrows 19005 are also shown. In each strand of wires, the wires may, for example, be intertwined to create a stable strand. The wires may, for example, be made from Nitinol, and this configuration may be achieved, for example, by cutting two wires at a transition between a cable and mesh (although this may involve another manufacturing step). As shown in FIG. 15, which represents a general view of an exemplary intraluminal device 15000 in accordance with the present disclosure, the strands may cross each other to create large openings (cells). In the intersections, for example, the strands may be intertwined with one another to create a loosely coupled junction. Before and after the junction, for example, the wires of the strands may be intertwined.

As shown in FIG. 16, a strand of two wires (i.e., wires 16020) may cross a strand of three wires (i.e., wires 16010). The intertwined wires before and after the junction and the intertwining of the wires inside the junction may create a loosely coupled but stable junction and cross-section, which helps prevent slippage and create large cells, ultimately helping to resist collapse of the device when expanded with high radial force within a tube. And, as shown in FIGS. 17-18 (where FIG. 17 is a detail of region 16015 of FIG. 16 in an expanded configuration, and FIG. 18 is a detail of FIG. 15 in an expanded configuration), when the mesh is expanded, the junction structure keeps the wires together even when the mesh is expanded. As a result, the mesh size remains the same.

Figure 19B:
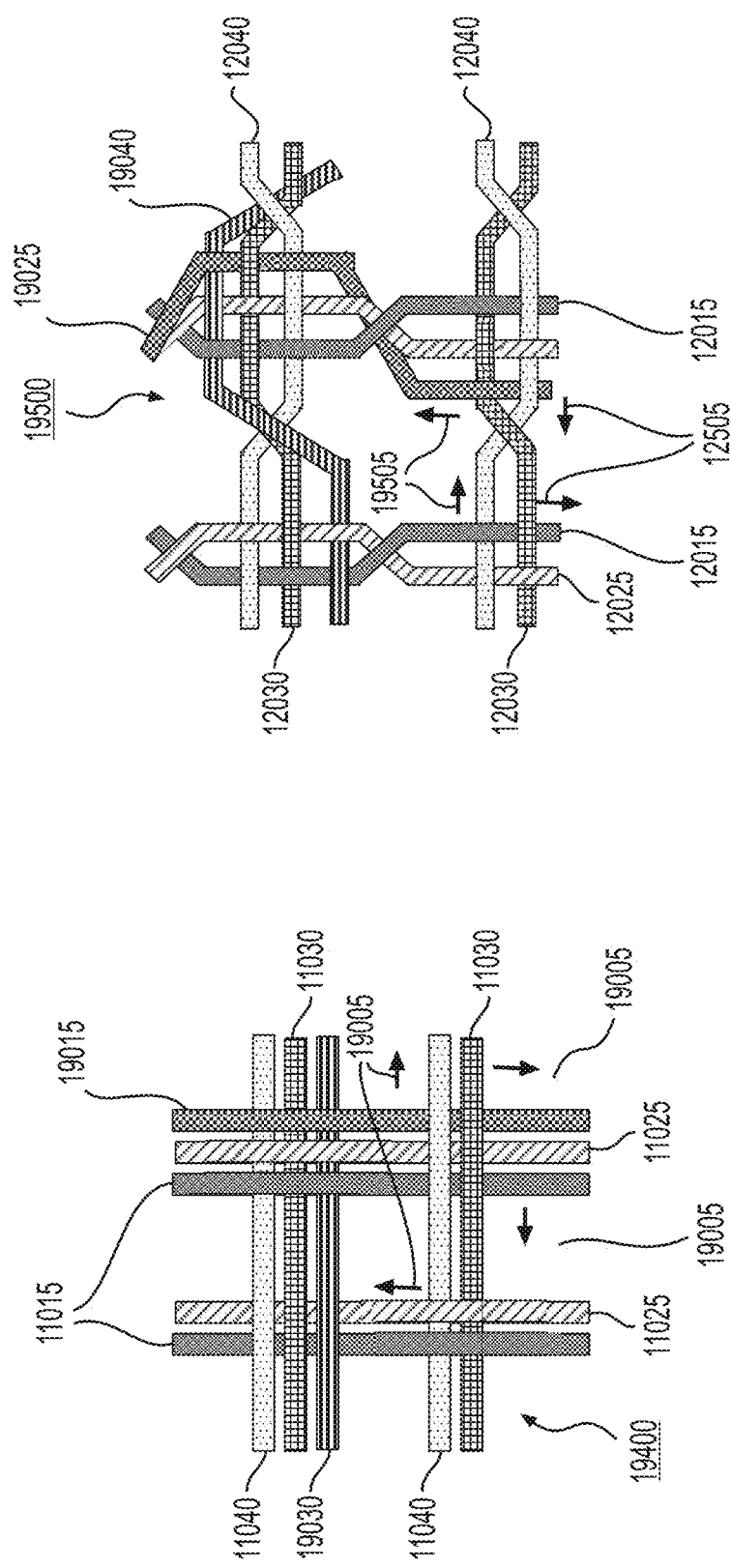
Figure 19C:
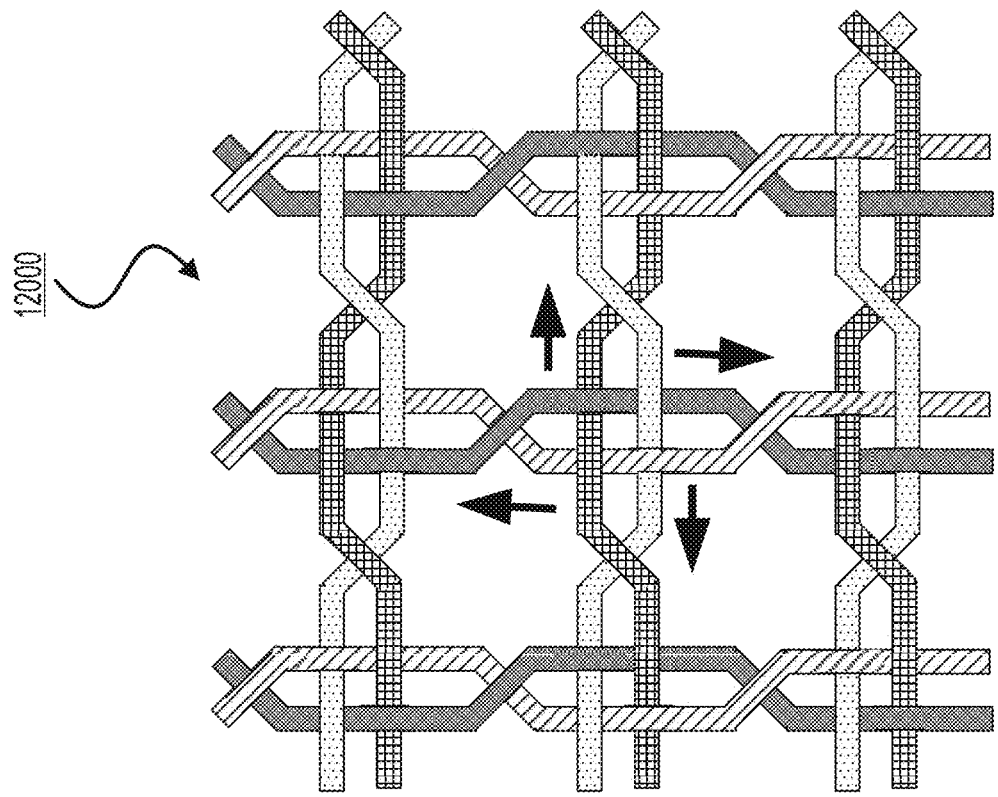
Figure 19C:
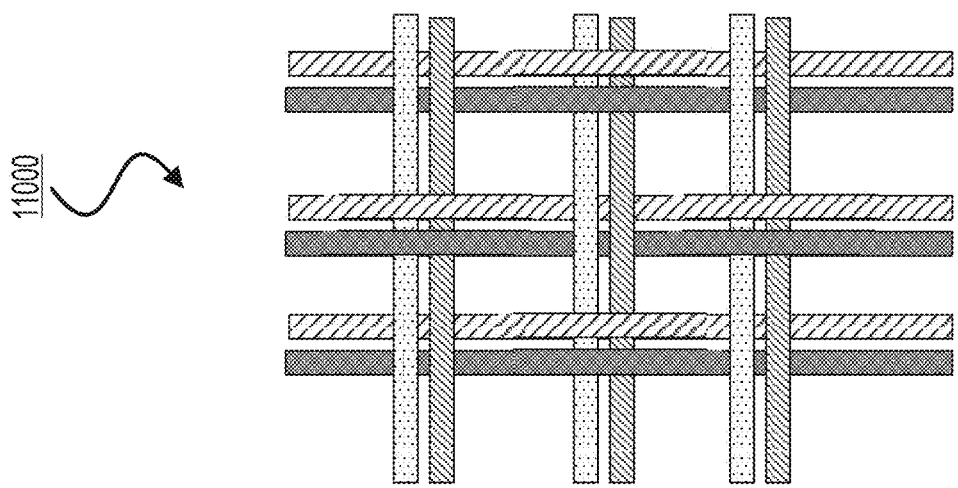

FIGS. 19A-C illustrate 8-, 10-, and 12-wire junctions and configurations. In addition, as discussed above, devices 15000 and 18000, and the detailed views of FIGS. 16 and 17 may use the 12-wire junctions of FIGS. 19A and 19C. Of course, these are only examples, and the wire junctions and configurations with more or less wires may be used, and that regardless of the number of wires, differing braiding arrangements may be employed.

Figure 20:
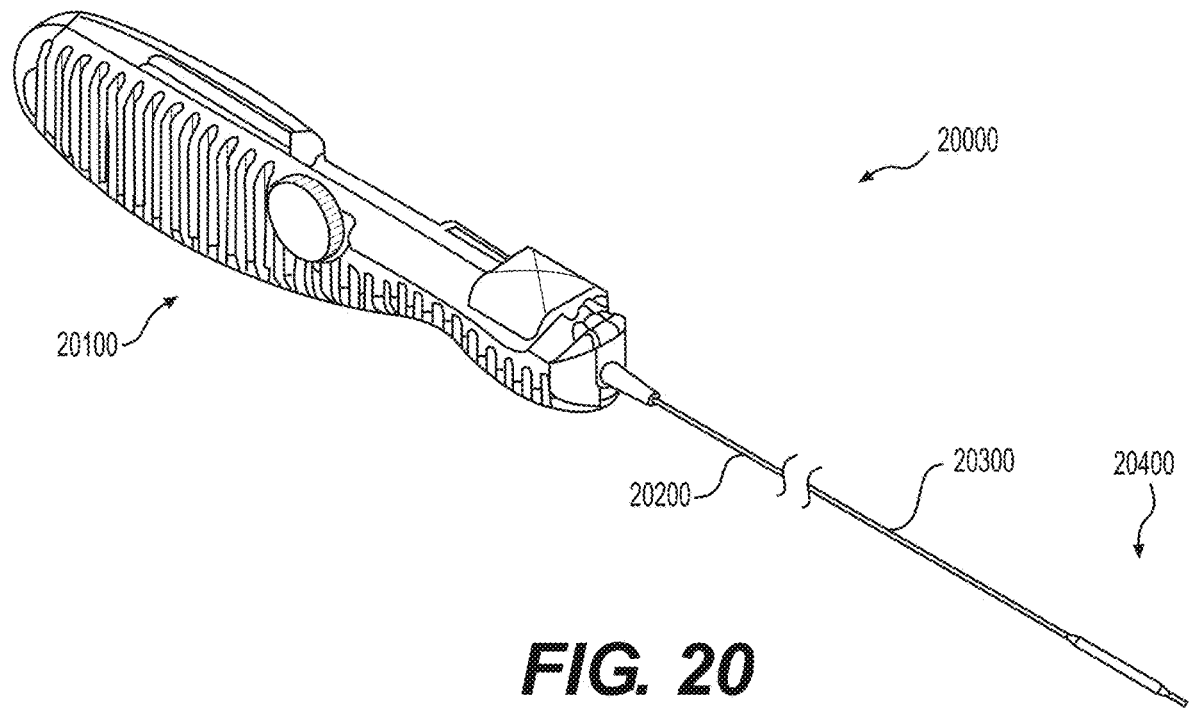
FIG. 20 is an illustration of another exemplary intraluminal device, in accordance with at least one of the disclosed embodiments.

As shown in FIG. 20, in accordance with at least some alternative embodiments of an intraluminal device 20000 in accordance with the present disclosure, the device 20000 may have the five following parts, for example:
a) a control handle 20100;
b) a stiff proximal shaft 20200, such as a stainless steel hypotube;
c) a flexible shaft 20300 (made from a cable of wires, for example);
d) clot engaging component 20400, such as an clot engaging expandable mesh and/or an clot anchor platform which is made from the same wires of the cable of flexible shaft 20300; and
e) a corewire or control wire (not shown in FIG. 20) which may be connected to the distal tip of the mesh of clot engaging component 20400 and which runs through the shafts 20200, 20300 to the handle 20100.

As shown in FIGS. 21A-B and 22A-C, in accordance with at least some embodiments of an intraluminal device 20000 in accordance with the present disclosure, the clot engaging component 20400 of intraluminal device 20000 may include a clot anchoring segment 21600 distal to a clot engaging mesh 21400, configured to engage hard clots 21800. The clot anchoring segment 21600 may be manually adjustable and/or self-expandable. In some embodiments, clot anchoring segment 21600 may be heat-treated such that it is configured to expand radially outward when released from catheter 21700. According to various embodiments in which clot anchoring segment 21600 is manually adjustable, its expansion may be controlled, at least in part, by a control wire. In some embodiments, the distal end of a control wire 21550 may be connected to a portion of clot anchoring segment 21600, such as the distal portion thereof. In some embodiments, proximal clot engaging mesh 21400 and clot anchoring segment 21600 may be a unitary structure or may be connected together, such that a force (e.g., a pulling force) exerted upon clot anchoring segment 21600 by the control wire 21550 may transfer to clot engaging mesh 21400, causing simultaneous adjustment of clot anchoring segment 21600 and proximal clot engaging mesh 21400. According to various embodiments in which clot anchoring segment 21600 is self-expanding, a control wire 21500 may be connected to a portion of proximal clot engaging mesh 21400, such as the distal end thereof.

In accordance with alternative embodiments, the intraluminal device may have two or more control wires which run through the shafts 20200, 20300 and which may be connected to a handle 20100. A first control wire 21500 may be connected to proximal clot engaging mesh 21400, such as the distal end thereof, and may be actuated to control expansion of proximal clot engaging mesh 21400. A second control wire 21550 may be connected to a portion of clot anchoring segment 21600, such as a distal end thereof, and may be actuated to control expansion of clot anchoring segment 21600.

Figure 22A:
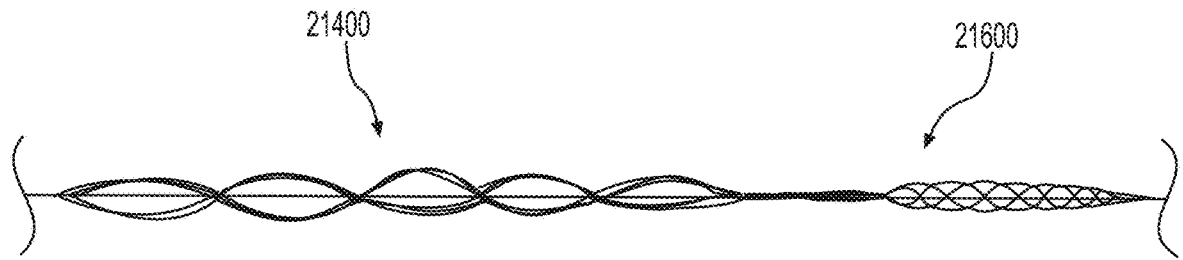
FIG. 22A is an illustration of another exemplary intraluminal device in a first exemplary position, in accordance with at least one of the disclosed embodiments.
Figure 22B:
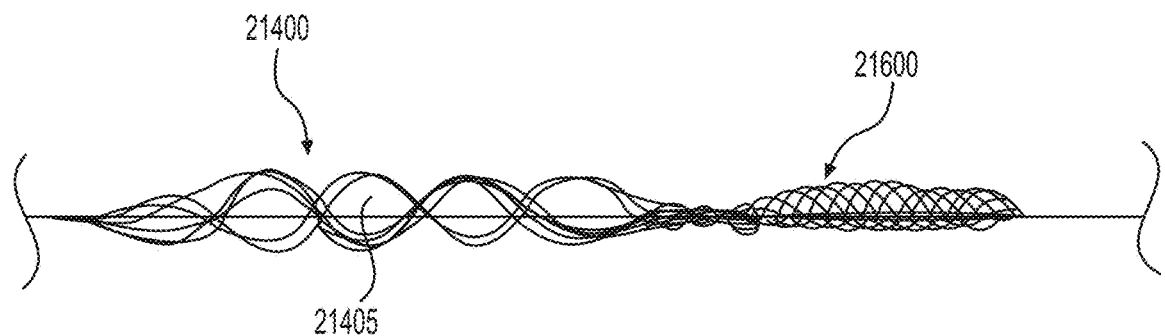
FIG. 22B is an illustration of the exemplary intraluminal device shown in FIG. 22A in a second exemplary position.
Figure 22C:
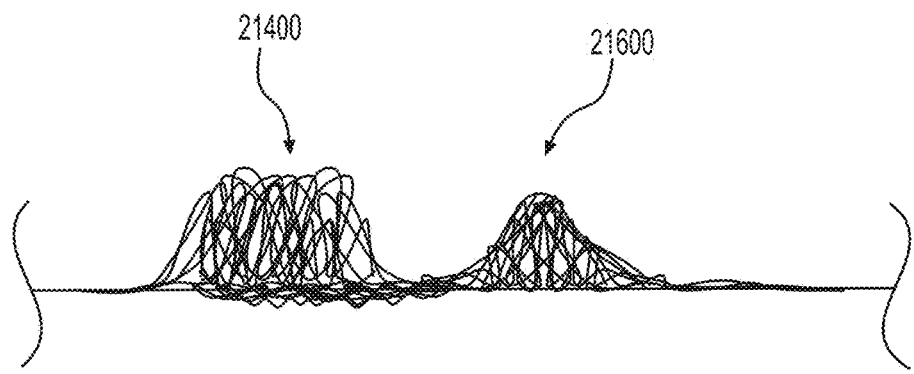
FIG. 22C is an illustration of the exemplary intraluminal device shown in FIG. 22A in a third exemplary position.

In accordance with at least some embodiments of the present disclosure, the outer diameter of proximal clot engaging mesh 21400 may be equal to or larger than the outer diameter of clot anchoring segment 21600 when they are in their respective retracted states. For example, FIG. 22A illustrates an embodiment in which proximal clot engaging mesh 21400 and clot anchoring segment 21600 are both retracted. Additionally or alternatively, the outer diameter of proximal clot engaging mesh 21400 may be equal to or larger than the outer diameter of clot anchoring segment 21600 when they are in their respective fully-expanded states. For example, FIG. 22C illustrates an embodiment in which proximal clot engaging mesh 21400 and clot anchoring segment 21600 are both fully expanded. As explained above, proximal clot engaging mesh 21400 may be configured for expansion independent of clot anchoring segment 21600, and vice versa. For example, FIG. 22B illustrated an embodiment in which proximal clot engaging mesh 21400 is expanded while clot anchoring segment 21600 remains retracted. Proximal clot engaging mesh 21400 may include at least one pore 21405 which is larger than other openings in the intraluminal device, including pores of clot anchoring segment 21600. The at least one pore 21405 may form a clot capturing area, allowing capture of clots within proximal clot engaging mesh 21400. In various embodiments, proximal clot engaging mesh 21400 may be configured for at least partial penetration of a clot and for expansion within the clot, either via a self-expansion mechanism or by actuation of at least one control cable. Proximal clot engaging mesh 21400 may exert an outward radial force upon the clot, achieving fracture and/or capture of the clot.

Figure 21A:
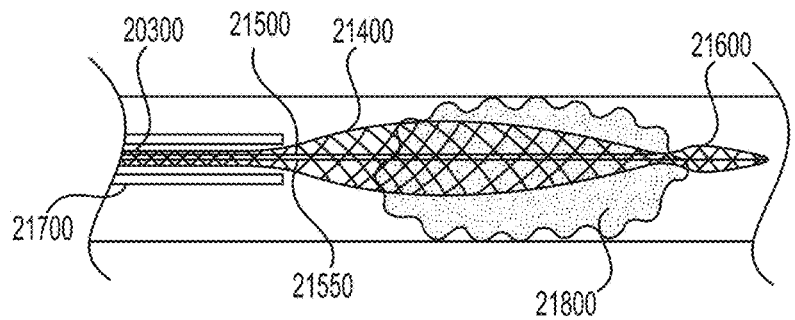
FIG. 21A is an illustration of another exemplary intraluminal device, in accordance with at least one of the disclosed embodiments.
Figure 21B:
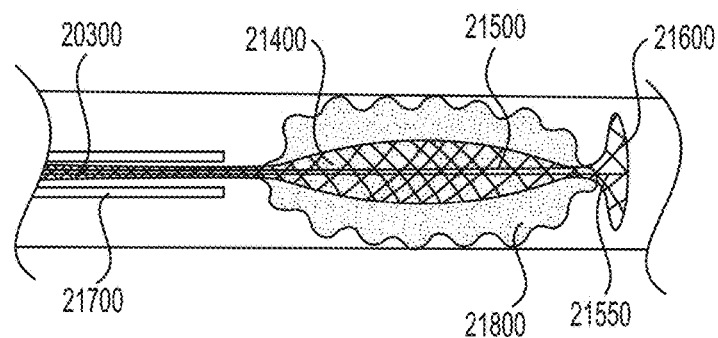
FIG. 21B is an illustration of the exemplary intraluminal device shown in FIG. 21A in an expanded position.

According to various embodiments, the distal end of intraluminal device 20000 may be configured to penetrate a clot. As illustrated in FIGS. 21A-B, proximal clot engaging mesh 21400 and clot anchoring segment 21600 may be pushed through clot 21800 until clot anchoring segment 21600 passes through the distal end of clot 21800 and is positioned within the portion of the vessel distal to the clot 21800. Proximal clot engaging mesh 21400 and clot anchoring segment 21600 may be configured to achieve small respective outer diameters when in their retracted states, such that they may penetrate and pass through clot 21800, such as by manipulation of handle 20100. Proximal clot engaging mesh 21400 may be expanded to capture the clot 21800. However, according to embodiments in which clot 21800 is too rigid for expansion of proximal clot engaging mesh 21400, clot anchoring segment 21600 may be expanded since it is positioned distal to the clot. According to some embodiments, the outer diameter of expanded clot anchoring segment 21600 may be smaller than the inner diameter of the blood vessel, such that clot anchoring segment 21600 does not contact the vessel wall. Alternatively, clot anchoring segment 21600 may be configured to expand until it contacts and conforms to the shape of the vessel wall. Expansion of clot anchoring segment 21600 may form a platform which may trap clot 21800 and prevent it from traveling distal to clot anchoring segment 21600. Once the intraluminal device 20000 is pulled proximally, clot anchoring segment 21600 may engage the clot 21800 and push it upstream. Any adhesion between the clot 21800 and the vessel may be overcome by the resultant shear forces. In some embodiments, partial expansion of proximal clot engaging mesh 21400 within clot 21800 may at least partially secure clot 21800 to proximal clot engaging mesh 21400. Once the clot is pushed proximally by clot anchoring segment 21600 and disengages from the vessel wall, the clot 21800 may be retrieved into the guiding catheter 21700. In some embodiments, at least one of proximal clot engaging mesh 21400 and clot anchoring segment 21600 may remain expanded until the clot 21800 is captured within catheter 21700.

As depicted in FIGS. 23A-B, 24, and 25, in accordance with at least some alternative embodiments of an intraluminal device 20000 in accordance with the present disclosure, the intraluminal device 20000 may include at least one clot anchoring segment and an expandable clot engaging mesh segment 23400 at the distal end thereof. The embodiment depicted in FIGS. 23A-B, 24, and 25 include three clot anchoring segments 23600, 23602, 23604. However, intraluminal device 20000 may include one, two, three, four, five, or more anchoring segments according to various embodiments. Clot engaging mesh segment 23400 may be manually expandable, such as by actuation of control wire 23550, and/or self-expanding, according to mechanisms discussed above, and may be configured to engage hard clots. According to some embodiments, clot anchoring segments 23600-23604 may be expanded by a single control wire 23500 that is connected to the most distal end of these segments, such as the distal-most segment 23604. Alternatively, each clot anchoring segment 23600, 23602, 23604 may be controlled by a respective control wire, which may be connected to the distal end of its respective clot anchoring segment. The respective outer diameters of clot anchoring segments 23600-23604 may be substantially equal in when the retracted state. When in the retracted state, the outer diameter of clot engaging mesh segment 23400 may be equal to or larger than the outer diameter of at least one of clot anchoring segments 23600-23604 when in the retracted state.

Figure 23A:
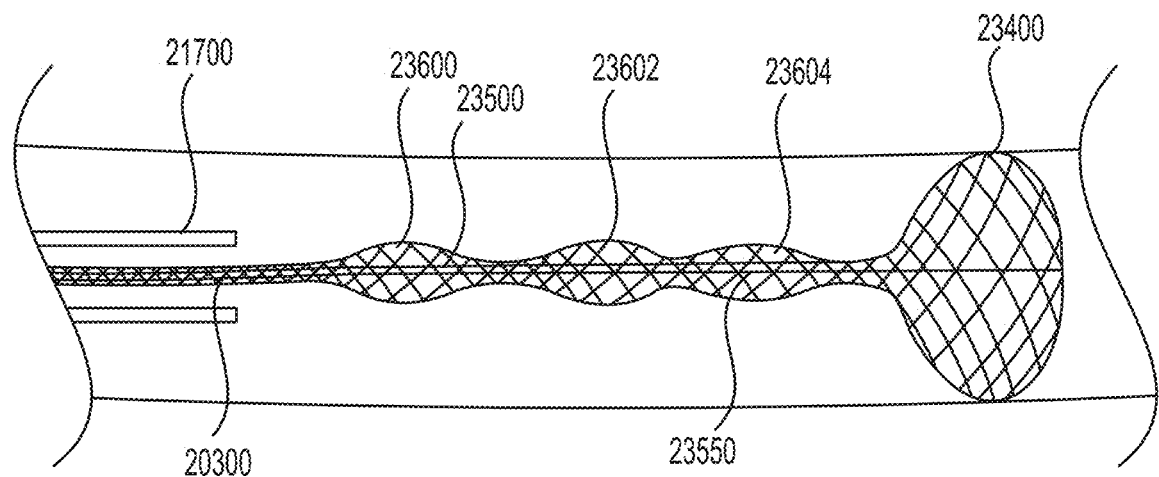
FIG. 23A is an illustration of another exemplary intraluminal device, in accordance with at least one of the disclosed embodiments.
Figure 23B:
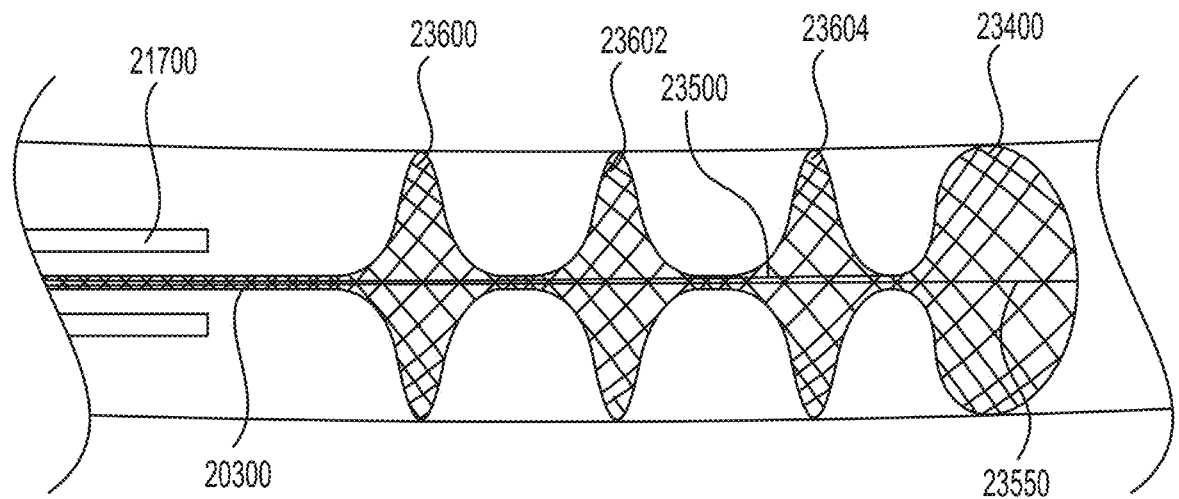
FIG. 23B is an illustration of the exemplary intraluminal device shown in FIG. 23A in an expanded position.
Figure 24:
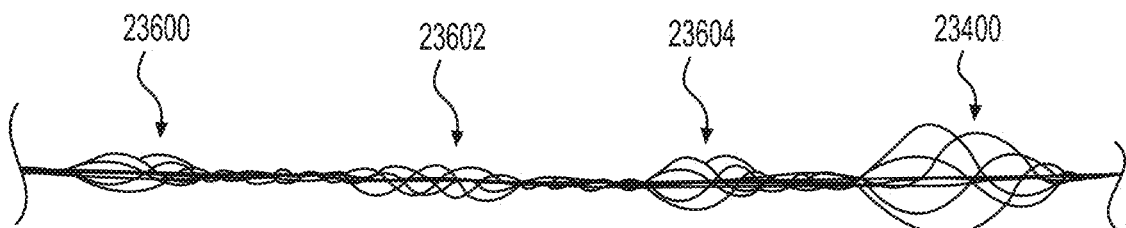
FIG. 24 is an illustration of another exemplary intraluminal device, in accordance with at least one of the disclosed embodiments.
Figure 25:
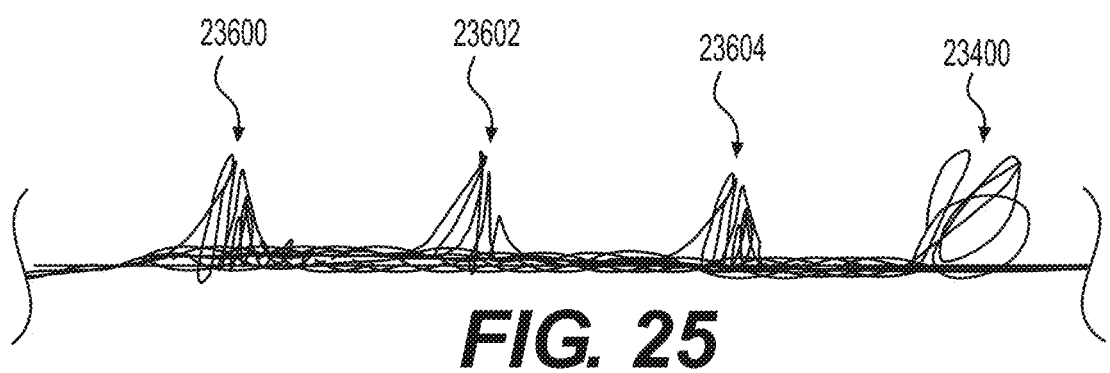
FIG. 25 is an illustration of another exemplary intraluminal device, in accordance with at least one of the disclosed embodiments.

As illustrated in FIG. 23B, the clot anchoring segments 23600-23604 may be expanded with high radial forces, each forming a platform configured to substantially prevent passage of clots thereby. According to some embodiments, the outer diameters of expanded clot anchoring segments 23600-23604 may be substantially equal and smaller than the inner diameter of the blood vessel, such that the clot anchoring segments 23600-23604 do not contact the vessel wall. According to alternative embodiments, clot anchoring segments 23600-23604 may be configured to expand until each contacts and conforms to the shape of the vessel wall. In still further embodiments, clot anchoring segments 23600-23604 may be configured for varying outer diameters when fully expanded. In some embodiments, proximal-most segment 23600 may have the largest expanded outer diameter and distal-most segment 23604 may have the smallest expanded outer diameter. In other embodiments, proximal-most segment 23600 may have the smallest expanded outer diameter and distal-most segment 23604 may have the largest expanded outer diameter. In still further embodiments, one or two of segments 23600-23604 may have expanded outer diameters which do not contact the vessel wall, while the remaining segments are configured to expand until they contact and conform with the vessel wall. Clot engaging mesh segment 23400 may be configured to have an outer expanded diameter which is equal to or larger than the expanded outer diameters of clot anchoring segments 23600-23604. Clot engaging mesh segment 23400 may be configured to self-expand independently of clot anchoring segments 23600-23604. For example, FIG. 24 illustrates an embodiment in which clot anchoring segments 23600-23604 are retracted and clot engaging mesh segment 23400 is expanded. While FIG. 25 illustrates an embodiment in which clot anchoring segments 23600-23604 and clot engaging mesh segment 23400 are all expanded.

When expanded, clot anchoring segments 23600-23604 may each form a platform with a larger outer diameter than that of any adjoining section between clot anchoring segments. For example, the transition between clot anchoring segment and adjoining section may be steep so as to form a shelf or seat capable of seating against a portion of a clot. The clot may be trapped between adjacent platforms, and then pushed (or pulled) as the device is retrieved proximally. As shown in FIGS. 23A-B, the clot engaging mesh segment 23400 (which can function as a distal self-expanding filter) may be configured to catch any detached clot fragments to secure a clean pass.

According to some embodiments, the intraluminal device may be delivered into a blood vessel, in proximity to a blood clot. Clot anchoring segments 23600-23604 and clot engaging mesh segment 23400 may be in their retracted states during delivery. The intraluminal device may be positioned such that clot engaging mesh segment 23400 is positioned distal to the clot location, with the clot positioned distal to at least one of clot anchoring segments 23600-23604. In some embodiments, the clot may be positioned proximal to proximal-most clot anchoring segment 23600. Additionally or alternatively, the clot may be positioned between two consecutive clot anchoring segments. Clot engaging mesh segment 23400 may self-expand or be expanded manually to catch any clot fragments distal to the clot anchoring segments. Before, during, or after expansion of clot engaging mesh segment 23400, the clot anchoring segments 23600-23604 may be expanded, either simultaneously or individually. In some embodiments, distal clot anchoring segment 23604 may be expanded first and proximal clot anchoring segment 23600 may be expanded last. Alternatively, in some embodiments, proximal clot anchoring segment 23600 may be expanded first and distal clot anchoring segment 23604 may be expanded last. Expansion of the clot anchoring segments 23600-23604 may form platforms which may trap the clot. The intraluminal device may be pulled proximally, causing the clot anchoring segments to push the clot proximally and into guiding catheter 21700. In some embodiments, at least one of clot anchoring segments 23600-23604 and clot engaging mesh segment 23400 may remain expanded until the clot is captured and removed from the vessel.

Figure 26A:
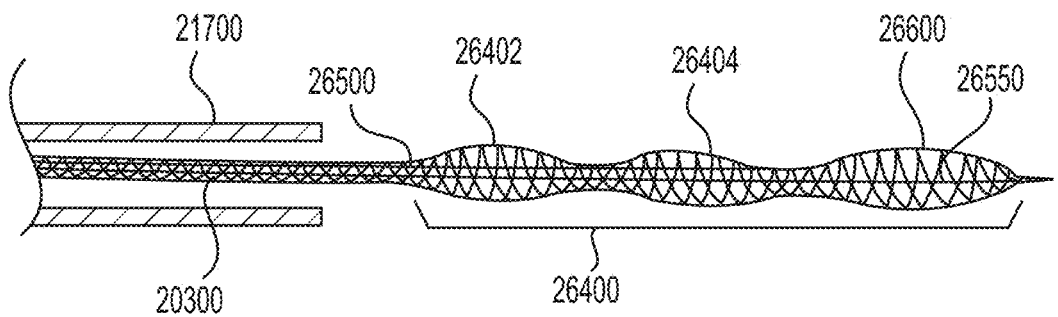
FIG. 26A is an illustration of another exemplary intraluminal device, in accordance with at least one of the disclosed embodiments.
Figure 26B:
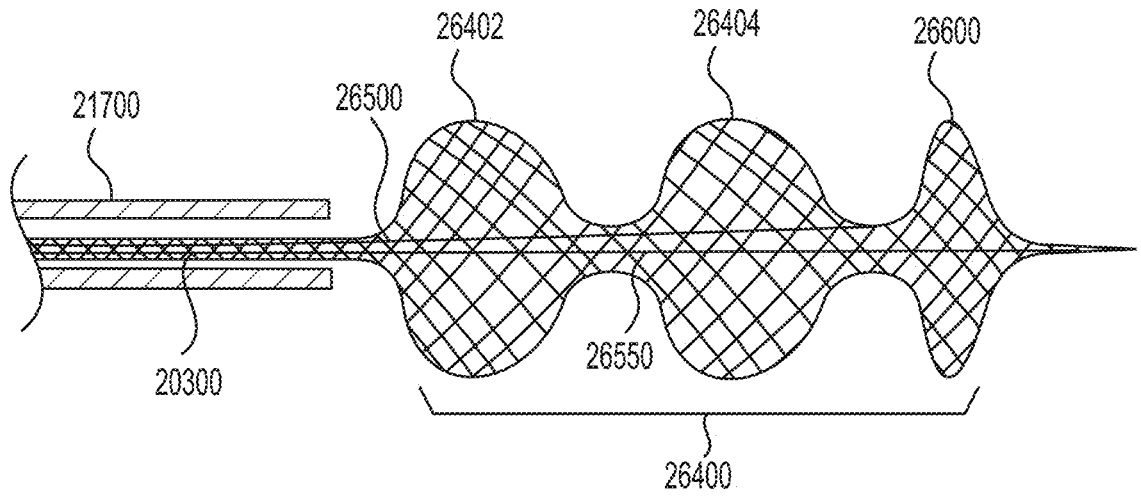
FIG. 26B is an illustration of the exemplary intraluminal device shown in FIG. 26A in an expanded position.

As depicted in FIGS. 26A-B, in accordance with another embodiment, the intraluminal device 20000 may include a long clot engaging segment 26400. The long clot engaging segment 26400 may include several sequential adjustable clot engaging mesh segments 26402 and 26404 to allow improved clot engagement where the clot has mixed hard and soft areas. In some embodiments, long clot engaging segment 26400 may include two, three, four five, or more adjustable clot engaging mesh segments. The clot engaging mesh segments 26402, 26404 can vary in radial force, wire arrangement, diameter, pore size, sparse and design. As a result, the clot engaging mesh segments 26402, 26404 may assume different sizes and/or shapes when expanded and may be configured to exert varying radial outward forces when expanded. The variation in force may be due, at least in part, to the wire arrangement (such as the braiding pattern), the pore size, and the segment length. In one embodiment, a first one of the clot engaging mesh segments 26402, 26404 may be expanded within a clot location. In the event that the segment exerts insufficient force to engage the clot, the first segment may be retracted, the device repositioned, and a second, more rigid clot engaging mesh segment may be expanded to penetrate and capture the clot. In another embodiment, when a first clot engaging mesh segment exerts insufficient outward force to expand and engage a clot, at least one other clot engaging mesh segment may be expanded to engage the clot in a softer area.

As also illustrated in FIGS. 26A-B, in accordance with at least some embodiments of an intraluminal device 20000 in accordance with the present disclosure, at least one distal adjustable clot anchor 26600 may be arranged at the distal end of the intraluminal device. Clot anchor 26600 may be configured to expand with high radial force, forming a platform at the distal end of the device. For example, clot anchor 26600 may be configured to expand until it contacts and conforms with the vessel wall. Once the intraluminal device is pulled proximally, the expanded clot anchor 26600 may engage the clot and push it proximally, in case that the clot engaging mesh segments 26402, 26404 did not capture the clot or a portion thereof. In some embodiments, at least one of clot engaging mesh segments 26402, 26404 and adjustable clot anchor 26600 may remain expanded until the clot is captured and removed from the vessel. Furthermore, a control wire 26550 may be attached to the distal-most anchoring segment 26600, and/or one or more control wires (such as control wire 26500) may be attached to the distal portion of one or more clot engaging mesh segments 26402 and 26404. Such control wires may be actuated to expand and retract their respective segment(s) as discussed throughout.

Figure 27:
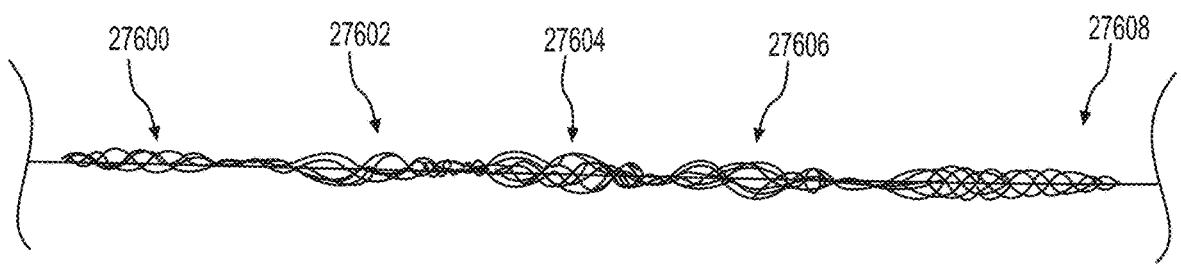
FIG. 27 is an illustration of another exemplary intraluminal device, in accordance with at least one of the disclosed embodiments.
Figure 28:
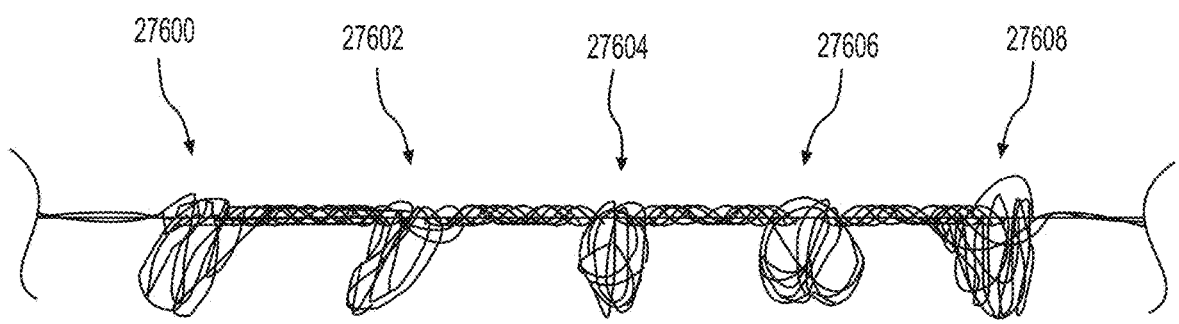
FIG. 28 is an illustration of another exemplary intraluminal device, in accordance with at least one of the disclosed embodiments.

As depicted in FIGS. 27-28, in accordance with another embodiment, the intraluminal device 20000 may include several adjustable clot anchoring segments 27600-27608, each of which may be configured to change its respective configuration to consequent platforms when expanded, to allow clot entrapment between the platforms. The intraluminal device may include two, three, four, five, six, seven, eight, nine, ten, or more clot anchoring segments. The clot anchoring segments 27600-27608 may vary in radial force, wire arrangement, diameter, pore size, sparse and design, for example. In some embodiments, each clot anchoring segment 27600-27608 may include a respective control wire, such that the segments may be individually expanded. In other embodiments, a single or multiple control wires may be attached to the distal-most clot anchoring segment and may be actuated to simultaneously expand all clot anchoring segments 27600-27608. In one embodiment, a first one of the clot anchoring segments 27600-27608 may be expanded distal to a clot location, so as to capture the clot. In the event that the clot anchoring segment does not capture the clot or at least a fragment thereof, a second clot anchoring segment may be expanded, for example distal to the first clot anchoring segment, to capture the remaining fragments of the clot. In some embodiments, the second clot anchoring segment may have a larger expanded outer diameter than the first clot anchoring segment and/or exert greater outward force than the first clot anchoring segment when expanded. For example, the second clot anchoring segment may be configured to expand until it contacts and conforms to the shape of the vessel wall. Advantageously, this may permit any clot fragments not captured by the first clot anchoring segment to be captured by the second clot anchoring segment. According to other embodiments, two or more of clot anchoring segments 27600-27608 may be expanded simultaneously, thus capturing the clot and any fragments thereof. Once the device is pulled proximally, the platforms formed by clot anchoring segments 27600-27608 may engage the clot and any fragments thereof and push it proximally. The platforms may also act as a filter, catching detached clot fragments. In some embodiments, at least one of clot anchoring segments 27600-27608 may remain expanded until the clot is captured and removed from the vessel.

Figure 29A:
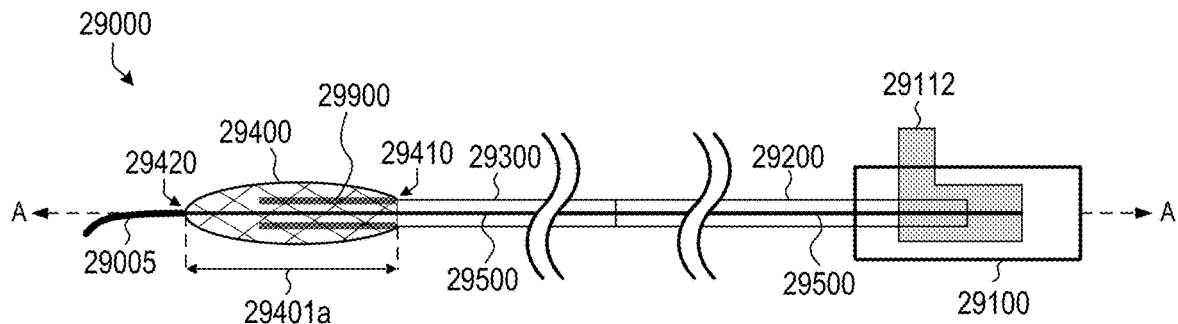
FIGS. 29A and 29B illustrate another exemplary intraluminal device, in accordance with at least one of the disclosed embodiments.
Figure 29B:
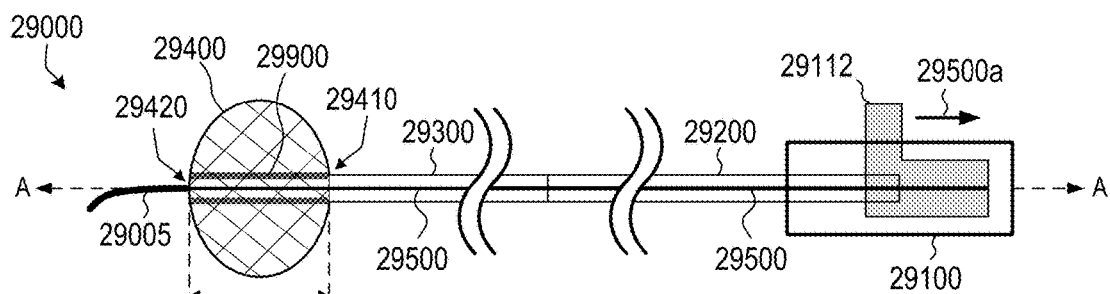

FIGS. 29A and 29B illustrate an exemplary intraluminal device 29000. Intraluminal device 29000 may include a control handle 29100, a proximal shaft portion 29200 extending from the distal end of the control handle 29100, and a distal shaft portion 29300 extending from, or otherwise connected to, the distal end of proximal shaft portion 29200. Proximal shaft portion 29200 and distal shaft portion 29300 may form a hollow, elongated shaft of intraluminal device 29000 extending along a longitudinal axis A of the intraluminal device. In some embodiments, proximal shaft portion 29200 may include a rigid hypotube (e.g., a stainless steel hypotube). Additionally, or alternatively, distal shaft portion 29300 may be configured to be more flexible than proximal shaft portion 29200. For example, in some embodiments, distal shaft portion 29300 may include a cable constructed of a plurality of flexible wires, which may extend into expandable mesh segment 29400 (which is described below). Optionally, a flexible atraumatic tip 29005 may be secured to the distal end of the intraluminal device 29000.

Intraluminal device 29200 may include an expandable mesh segment 29400 connected to, or otherwise situated distal to, the distal end of distal shaft portion 29300. Mesh segment 29400 may be formed by a plurality of wires that are woven or coiled to form the first mesh segment. In some embodiments, expandable mesh segment 29400 may include one or more of the exemplary wire arrangements (i.e., wire braiding patterns) discussed above. For example, at least a portion of mesh segment 29400 may be woven to form an exemplary clot capture section that is configured to capture and remove occlusive material (e.g., blood clots) from body lumens. Additionally, or alternatively, at least a portion of mesh segment 29400 may be woven to form an exemplary clot anchoring segment configured to form a platform that may trap an occlusion and, when pulled proximally, may engage the occlusion and push it upstream. Additionally, or alternatively, at least a portion of mesh segment 29400 may be woven to form a structure configured to assist in an aneurism coiling procedure and/or for treating vasospasm.

Mesh segment 29400 may be configured for radial expansion and contraction between a radially-contracted state (e.g., the state illustrated in FIG. 29A) and a radially-expanded state (e.g., the state illustrated in FIG. 29B). When the mesh segment 29400 is in the radially-contracted state, the distal end 29420 of the mesh segment may be spaced a first distance 29401*a* from the proximal end 29410 of the mesh segment. In some embodiments, mesh segment 29400 may have a first distance 29401*a* of between approximately 20.0 mm and approximately 100.0 mm. In some embodiments, the outer diameter of the mesh segment 29400 may be small when the mesh segment 29400 is in the radially-contracted state so that the mesh segment 29400 may be retained within a delivery device (e.g., delivery catheter 21700). For example, mesh segment 29400 may have an outer diameter of between approximately 0.5 mm and approximately 2.0 mm when the mesh segment 29400 is in the radially-contracted state. When the mesh segment 29400 is in the radially-expanded state, the outer diameter of the mesh segment 29400 may be larger than when the mesh segment 29400 is in the radially-contracted state. For example, mesh segment 29400 may be configured to radially expand until the mesh contacts the inner surface of a body lumen 29820 (e.g., a blood vessel). When the mesh segment 29400 is in the radially-expanded state, the distal end 29420 of the mesh segment may be spaced a second distance 29401*b* from the proximal end 29410 of the mesh segment; the second distance 29401*b* may be smaller than the first distance 29401*a*.

Exemplary intraluminal device 29000 may also include a core wire 29500, which may be connected to a portion of the expandable mesh segment 29400 and may extend through the distal shaft portion 29300 and proximal shaft portion 29200 to the control handle 29100. In some embodiments, core wire 29500 may be secured to the distal end 29420 of the expandable mesh segment 29400; additionally, or alternatively, core wire 29500 may be secured to a different portion of the expandable mesh segment 29400. Core wire 29500 may be secured to a wire actuator 29112 in the control handle 29100, which may be configured to effect axial movement of the core wire 29500 relative to the distal shaft portion 29300 and proximal shaft portion 29200. Wire actuator 29112 may include any appropriate mechanism for actuating axial movement of core wire 29500, examples of which include, but are not limited to, a rotatable knob, a wheel, a button, a slider, a lever, a joystick, a touchpad, and combinations thereof. Due to the connection between the core wire 29500 and mesh segment 29400, axial movement of the core wire 29500 (e.g., due to actuation of wire actuator 29112) may control movement of the mesh segment 29400 between the radially-contracted state and the radially-expanded state of the mesh segment by adjusting the distance between the proximal end 29410 and distal end 29420 of the mesh segment 29400. For example, in embodiments in which core wire 29500 is connected to the distal end 29420 of the mesh segment, proximal movement of core wire 29500 (represented by arrow 29500*a*) may pull the distal end 29420 of the mesh segment towards the proximal end 29410 of the mesh segment, causing the mesh segment 29400 to radially expand.

Figure 29C:
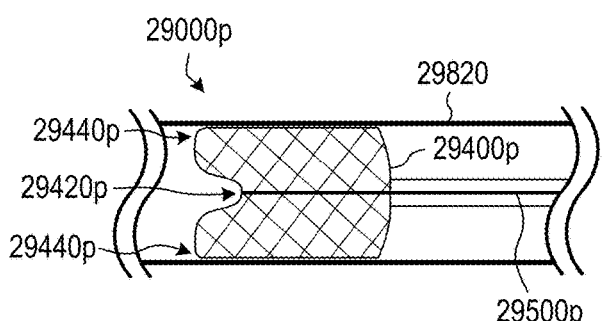
FIG. 29C is an illustration of a prior art intraluminal device expanded within a body lumen.

FIG. 29C illustrates a problem experienced by prior art mesh segments (represented as mesh segment 29400*p*) when the mesh segments are expanded within a hollow body lumen 29820 or within a hollow device (e.g., catheter 21700) due to actuation of a core wire 29500*p*. As illustrated in FIG. 29C, when the outer diameter of the mesh segment 29400*p* contacts the body lumen 29820, further actuation of the core wire 29500 causes a fold-back of the distal end of the mesh segment 29400*p* in which the distal end 29420*p* of the mesh segment is pulled proximally while the mesh outer edges 29440*p* are held in place due to their contact with body lumen 29820. Existing intraluminal meshes do not include any mechanism to prevent this folding-back effect. As a result, the fold-back can cause irreversible damage to the mesh segment 29400*p*, to the point that the intraluminal device 29000*p* may no longer be functional. In addition, fold-back of the mesh segment reduces the magnitude of the radial force exerted by the mesh segment on the body lumen and often limits, or even completely eliminates, the user's ability to control expansion and contraction of the mesh segment.

Figure 29D:
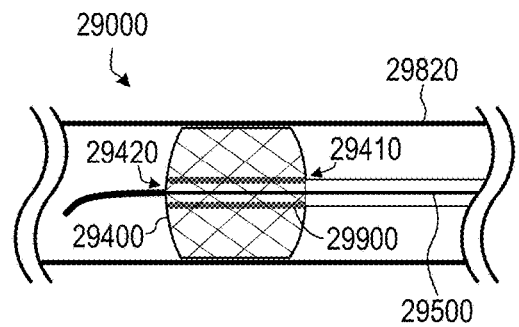
FIG. 29D is an illustration of the exemplary intraluminal device shown in FIGS. 29A and 29B expanded within a body lumen.

To prevent fold-back of the mesh segment 29400, exemplary intraluminal device 29000 may include at least one expansion limiter 29900 situated partially or entirely within the mesh segment 29400. The expansion limiter 29900 may include at least one lumen therethrough and may be contained within the mesh segment 29400, with the core wire 29500 passing through the expansion limiter 29900. The expansion limiter 29900 may be configured to hold the proximal end 29410 and distal end 29420 of the mesh segment apart by a minimum predetermined distance, such that radial expansion of the mesh segment 29400 beyond a predetermined diameter may be prevented. In some embodiments, the expansion limiter 29900 may be configured to hold the proximal end 29410 and distal end 29420 of the mesh segment apart by at least the second distance 29401*b*, such that the expansion limiter 29900 may, at least in part, limit the maximum outer diameter of the mesh segment 29400 in the radially-expanded state. As illustrated in FIG. 29D, the expansion limiter 29900 may prevent fold-back of the mesh segment 29400 because once the proximal end 29410 and distal end 29420 of the mesh segment reach the minimum predetermined distance (e.g., second distance 29401*b*), further proximal advancement of the distal end 29420 due to actuation of the core wire 29500 is prevented by the expansion limiter 29900.

In some embodiments, the expansion limiter 29900 may be devoid of permanent connection to other elements of the intraluminal device 29000; instead, it may be held in place due to its placement within the expandable mesh segment 29400. In alternative embodiments, expansion limiter 29900 may be connected to one or more portions of the mesh segment 29400, such as the proximal end 29410 and/or the distal end 29420. Additionally, or alternatively, expansion limiter 29900 may be secured to the distal end of distal shaft portion 29300. The expansion limiter 29900 may be constructed of an alloy or metal (e.g., nickel-titanium alloy), stainless steel, a polymer, and/or another suitable material. In some embodiments, the expansion limiter 29900 may have an outer diameter of between approximately 0.12 mm and approximately 0.25 mm.

In some embodiments, the expansion limiter 29900 may include a hollow, cylindrical tube constructed of a material such as stainless steel or nickel-titanium alloy. The hollow tube may be laser-cut, so as to allow the expansion limiter 29900 to be sufficiently pliable to bend through tortuous anatomy during delivery of the intraluminal device 29000 to a treatment site within the body. In some embodiments, the hollow tube of the expansion limiter 29900 may have an axial length of between approximately 5.0 mm and 20.0 mm. Accordingly, mesh segment 29400 may have a second distance 29401*b* of between approximately 5.0 mm and 20.0 mm, in some embodiments. In some embodiments, the hollow tube of the expansion limiter 29900 may contact both the proximal end 29410 and distal end 29420 of the mesh segment when the mesh segment is expanded (e.g., as depicted in FIGS. 29B and 29C), thus preventing further expansion of the mesh segment 29400. However, the hollow tube of the expansion limiter 29900 may not be in contact with one or both of the proximal end 29410 and distal end 29420 of the mesh segment when the mesh segment is radially-contracted (e.g., as depicted in FIG. 29A) due to the increased axial distance between the proximal end 29410 and distal end 29420 of the mesh segment.

Figure 30A:
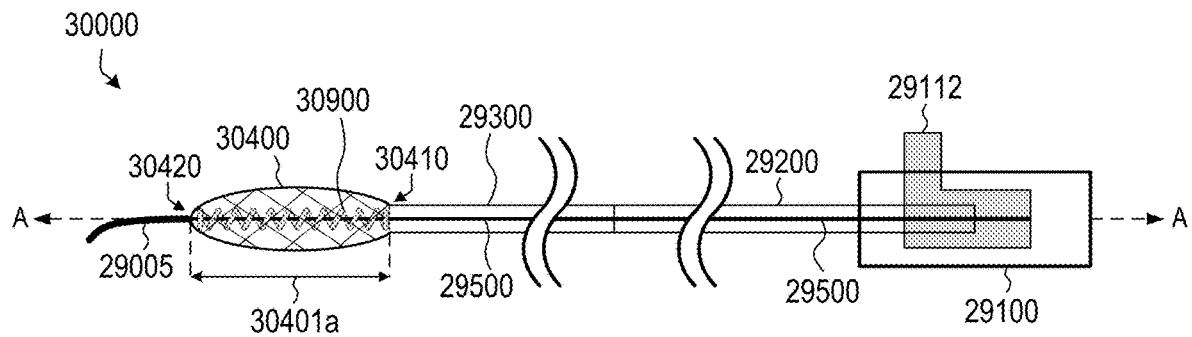
FIGS. 30A and 30B illustrate another exemplary intraluminal device, in accordance with at least one of the disclosed embodiments.
Figure 30B:
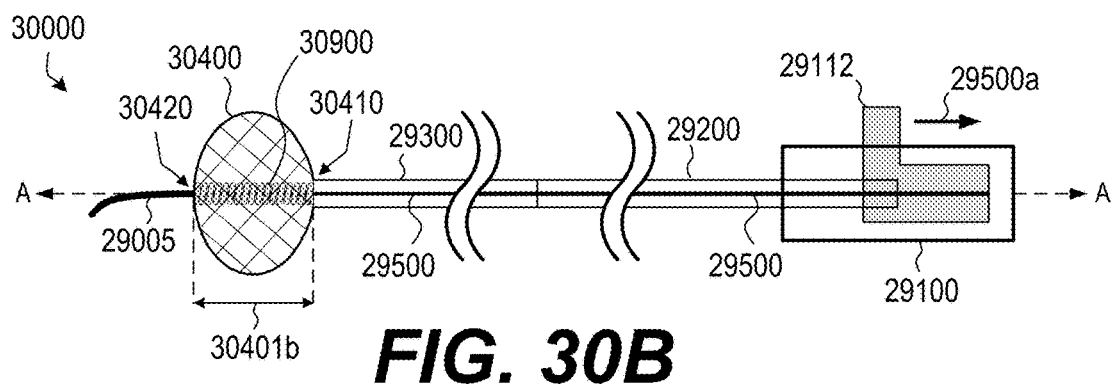
Figure 30C:
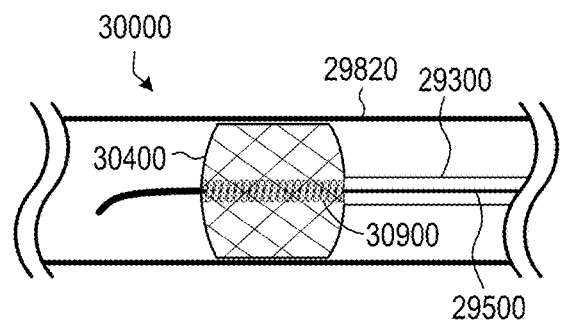
FIG. 30C is an illustration of the exemplary intraluminal device shown in FIGS. 30A and 30B expanded within a body lumen.

FIGS. 30A and 30B illustrate an exemplary intraluminal device 30000 that may be similarly configured as intraluminal device 29000, apart from including an alternative expansion limiter 30900 situated partially or entirely within the expandable mesh segment 30400. Expansion limiter 30900 may include an elastic, helical coil configured to axially stretch and contract between a free length (i.e., the axial length of the coil when no axial forces are exerted upon the coil) and a solid length of the coil i.e., the minimum axial length of the coil, beyond which the coil cannot be shortened). In some embodiments, the solid length of the helical coil of expansion limiter 30900 may be substantially equal to the second distance 30401*b*, such that the helical coil of expansion limiter 30900 may hold the proximal end 30410 and distal end 30420 of the mesh segment apart by at least the second distance 30401*b*. For example, the helical coil of expansion limiter 30900 may have a solid length of between approximately 5.0 mm and 20.0 mm. As illustrated in FIG. 30C, this configuration of the helical coil of expansion limiter 30900 may prevent fold-back during expansion of the mesh segment 30400 within a body lumen 29820 by holding the proximal and distal ends of the mesh segment 30400 apart by at least the second distance 30401*b*. In some embodiments, the expansion limiter 30900, including the helical coil, may have an outer diameter of between approximately 0.12 mm and approximately 0.25 mm.

In some embodiments, the helical coil of expansion limiter 30900 may have a free length that is longer than the second distance 30401*b* and shorter than the first distance 30401*a*. In such embodiments, the helical coil may not contact the proximal end 30410 and distal end 30420 of the mesh segment when the mesh segment 30900 is in the radially-contracted state. In some alternative embodiments, the helical coil of expansion limiter 30900 may have a free length that is longer than both the second distance 30401*b* and the first distance 30401*a*. In such embodiments, the helical coil may be in contact with the proximal end 30410 and distal end 30420 of the mesh segment, and may be at least partially compressed, at all degrees of expansion of the mesh segment 30900. Accordingly, the helical coil may be biased to hold the proximal end 30410 and distal end 30420 of the mesh segment apart by at least the first distance 30401*a*. In further alternative embodiments, the helical coil of expansion limiter 30900 may have a free length that is equal to the first distance 30401*a*. In such embodiments, the helical coil may be in a non-compressed state when the mesh segment 30900 is in the radially-contracted state and may also contact the proximal end 30410 and distal end 30420 of the mesh segment when the mesh segment 30900 is in the radially-contracted state.

Figure 31A:
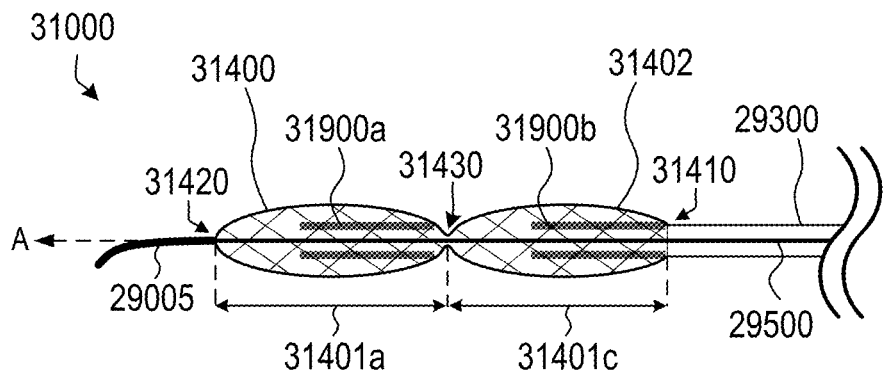
FIGS. 31A-C illustrate another exemplary intraluminal device, in accordance with at least one of the disclosed embodiments.
Figure 31B:
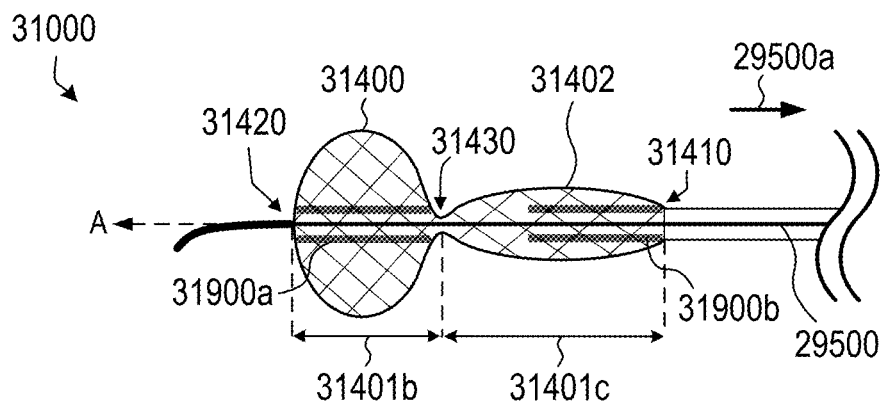
Figure 31C:
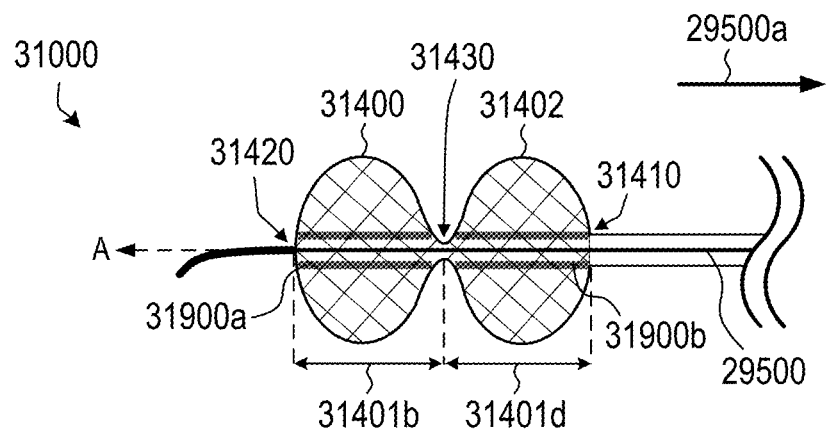

FIGS. 31A-C illustrate another exemplary intraluminal device 31000 having multiple radially-expandable mesh segments, each of which may be configured to expand from a radially-contracted state thereof to a radially-expanded state thereof. Although the example illustrated in FIGS. 31A-C includes two mesh segments 31400 and 31402, those of ordinary skill will understand that intraluminal device 31000 may include one mesh segment, two mesh segments, three mesh segments, four mesh segments, five mesh segments, or any other suitable number of mesh segments. The mesh segments 31400 and 31402 may extend between a mesh segment proximal end 31410 and a mesh segment distal end 31420 and may be separated by a transition zone 31430, which may be configured for minimal or no radial expansion. Core wire 29500 may extend through both mesh segments 31400 and 31402 and may be secured to a portion of the distal mesh segment 31400 (e.g., to mesh segment distal end 31420). Axial movement of core wire 29500 (e.g., under control of wire actuator 29112) may control expansion and contraction of both mesh segments 31400 and 31402 between their respective radially-contracted and radially-expanded states.

Mesh segments 31400 and 31402 may be configured for radial expansion and contraction between a radially-contracted state (FIG. 31A illustrates an example in which both meshes 31400 and 31402 are in a radially-contracted state) and a radially-expanded state (FIG. 31C illustrates an example in which both meshes 31400 and 31402 are in a radially-expanded state). When the distal mesh segment 31400 is in the radially-contracted state, the mesh segment distal end 31420 may be spaced a first distance 31401*a* from the transition zone 31430. Similarly, when the proximal mesh segment 31402 is in the radially-contracted state, the transition zone 31430 may be spaced a third distance 31401*c* from the mesh segment proximal end 31410. When the distal mesh segment 31400 transitions from the radially-contracted state to the radially-expanded state (e.g., due to axial movement of core wire 29500), the mesh segment distal end 31420 may be drawn proximally until it is spaced a second distance 31401*b* from the transition zone 31430, causing expansion of the distal mesh segment 31400. A distal expansion limiter 31900*a* may prevent further expansion of the distal mesh segment beyond the diameter corresponding to second distance 31401*b*. Similarly, when the proximal mesh segment 31402 transitions from the radially-contracted state to the radially-expanded state (e.g., due to axial movement of core wire 29500), the transition zone 31430 may be drawn proximally until it is spaced a fourth distance 31401*d* from the mesh segment proximal end 31420, causing expansion of the proximal mesh segment 31402. A proximal expansion limiter 31900*b* may prevent further expansion of the proximal mesh segment beyond the diameter corresponding to fourth distance 31401d. The first distance 31401a may be larger than the second distance 31401b, and the third distance 31401c may be larger than the fourth distance 31401d.

In some embodiments, mesh segments 31400 and 31402 may each include an expansion limiter 31900a and 31900b, respectively. Expansion limiters 31900a and 31900b may be configured as a hollow, cylindrical tube, as an elastic, helical coil, or may have any other suitable configuration. In the example depicted in FIGS. 31A-31C, expansion limiters 31900a and 31900b are configured as cylindrical tubes through which core wire 29500 may extend.

As illustrated in FIGS. 31A-C, mesh segments 31400 and 31402 may be expanded sequentially when a proximal force is applied by core wire 29500, with the distal-most mesh segment 31400 expanding first and the proximal-most mesh segment 31402 expanding last. In some embodiments, core wire 29500 may pull mesh segment distal end 31420 proximally towards transition zone 31430. As illustrated in FIG. 31B, this may cause radial expansion of distal mesh segment 31400, while proximal mesh segment 31402 may remain radially-contracted. This may occur because the proximal force exerted by the core wire 29500 is applied to the distal end of the distal mesh segment 31400, and minimal or no force is transmitted to proximal mesh segment 31402. Once the distal mesh segment 31400 is fully radially-expanded (i.e., once distal mesh segment 31400 has an axial length equal to second length 31410b and expansion limiter 31900a prevents further expansion of the distal mesh segment), the proximally-applied force from the core wire 29500 is then transferred to transition zone 31430 via the expansion limiter 31900a. The applied force then pulls transition zone 31430 proximally towards the mesh segment proximal end 31410, causing radial expansion of the proximal mesh segment 31402. This expansion may occur until the proximal mesh segment 31402 is fully radially-expanded (i.e., when proximal mesh segment 31402 has an axial length equal to fourth length 31410d and expansion limiter 31900b prevents further expansion of the proximal mesh segment). At this point, exemplary intraluminal device 31000 may be configured in the state illustrated in FIG. 31C; any additional proximally-directed force may be prevented from causing further expansion (and thus fold-back) of the mesh segments 31400 and 31402, since the expansion limiters 31900a and 31900b may hold mesh segments 31400 and 31402 at second distance 31401b and fourth distance 31401d, respectively. Advantageously, this sequential expansion mechanism may provide greater control over the expansion of the mesh segments 31400, 31402 because the specific order of mesh expansion is known. In addition, incorporation of the expansion limiters 31900a and 31900b may prevent foldback of all mesh segments, including the distal-most mesh segment 31400.

Figure 32A:
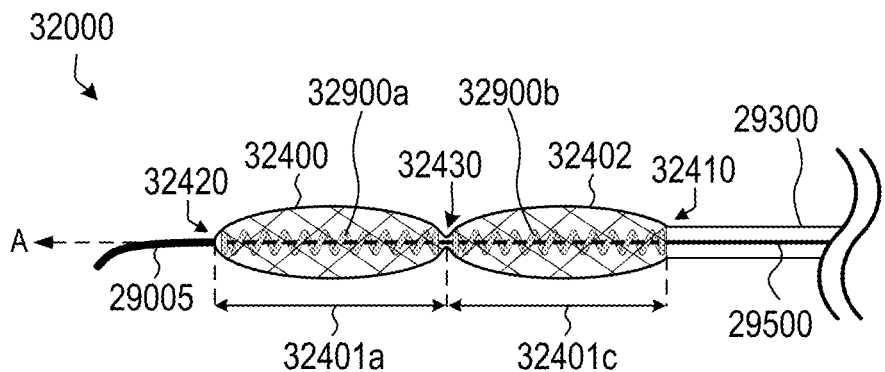
FIGS. 32A-C illustrate another exemplary intraluminal device, in accordance with at least one of the disclosed embodiments.
Figure 32B:
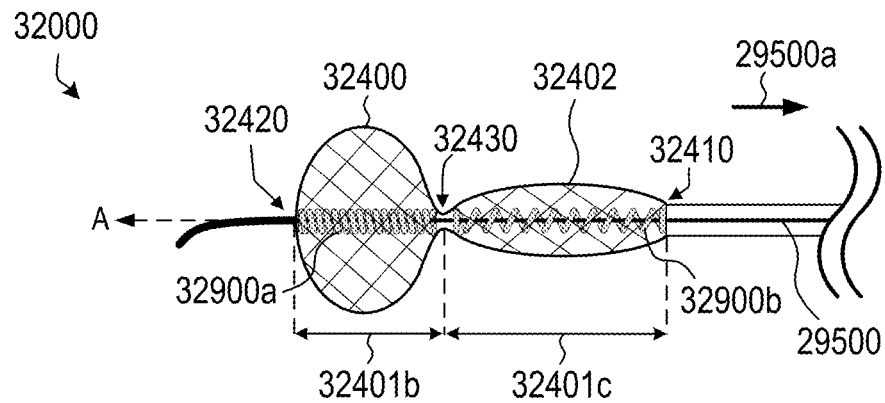
Figure 32C:
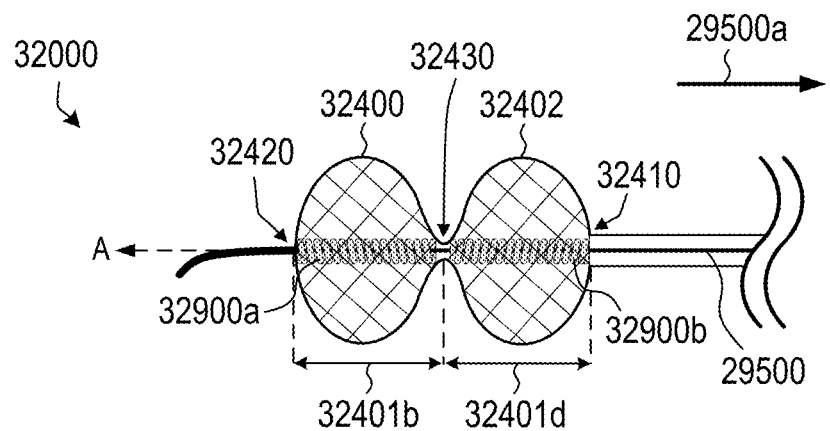

FIGS. 32A-C illustrate another exemplary intraluminal device 32000 having multiple radially-expandable mesh segments 31400, 31402 containing expansion limiters 32900a and 32900b, respectively. Expansion limiters 32900a and 32900b may each include an elastic, helical coil configured to axially stretch and contract between a free length and a solid length, as described above. Expansion limiters 32900a and 32900b may be configured to cause sequential expansion of mesh segments 31400 and 31402. FIG. 32A illustrates a state in which both mesh segments 31400 and 31402 are in a radially-contracted state. As shown in FIG. 32B, proximal movement of core wire 29500 exerts a radially-expanding force upon distal mesh segment 31400, while proximal mesh segment 31402 may remain radially-contracted. Upon full expansion of the distal mesh segment 31400, proximally-applied force may then be applied to transition zone 31430 via expansion limiter 32900a, causing radial expansion of proximal mesh segment 31402. Upon full expansion of the proximal mesh segment 31402, as illustrated in FIG. 32C, expansion limiters 32900a and 32900b may be configured to prevent further expansion, and thus fold-back, of mesh segments 31400 and 31402.

Figure 33A:
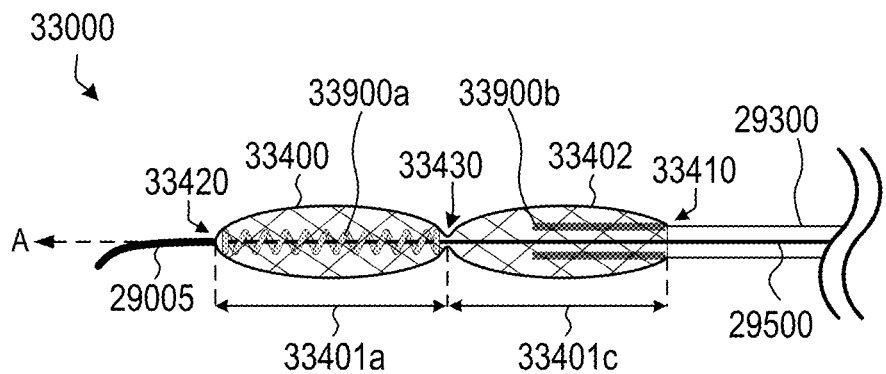
FIGS. 33A-C illustrate another exemplary intraluminal device, in accordance with at least one of the disclosed embodiments.
Figure 33B:
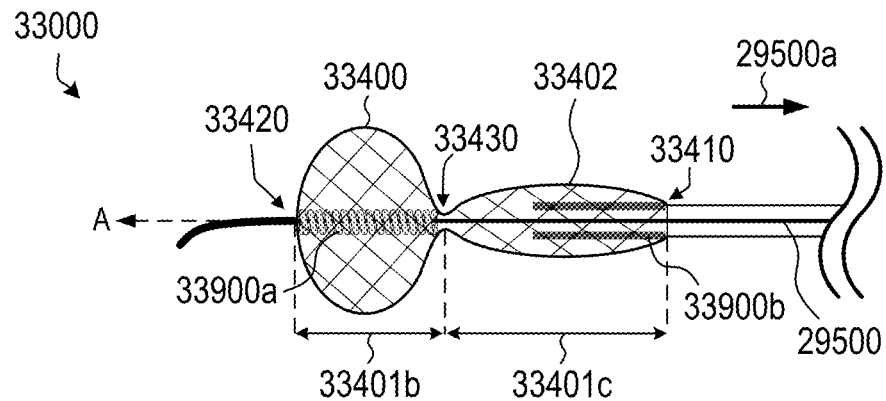
Figure 33C:
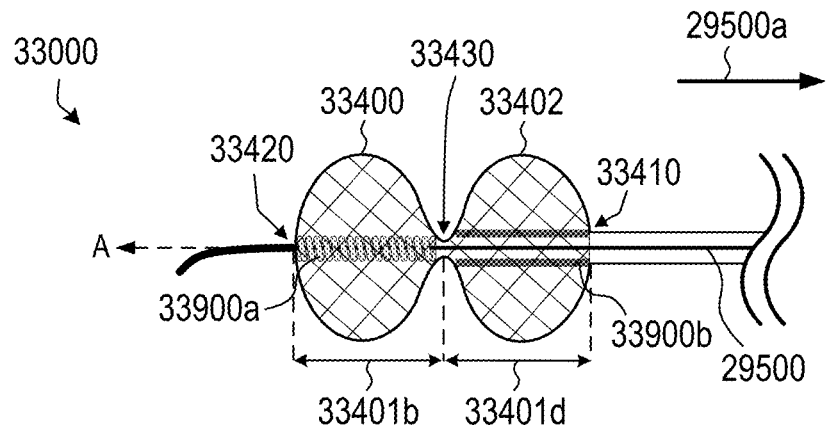

FIGS. 33A-C illustrate another exemplary intraluminal device 33000 having multiple radially-expandable mesh segments 31400, 31402 containing expansion limiters 32900a and 32900b, respectively. In the example of FIGS. 33A-C, the expansion limiters 32900a and 32900b may have different configurations. For example, one or more expansion limiters may be configured as a cylindrical tube, while one or more expansion limiters may be configured as a helical coil. Additionally, or alternatively, one or more expansion limiters may have some other suitable configuration.

Figure 34A:
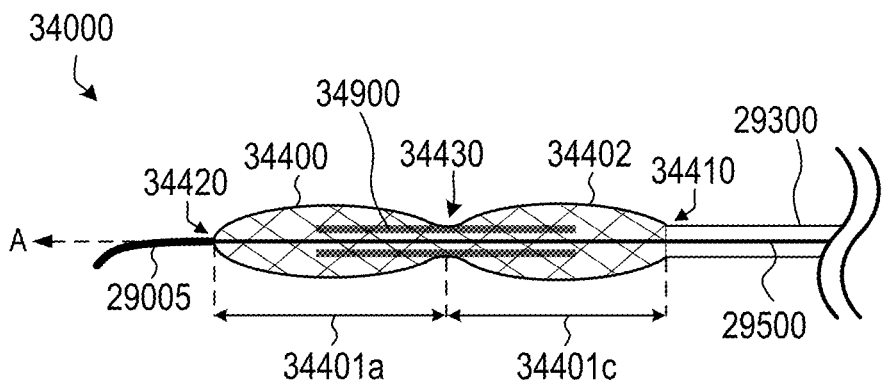
FIGS. 34A-C illustrate another exemplary intraluminal device, in accordance with at least one of the disclosed embodiments.
Figure 34B:
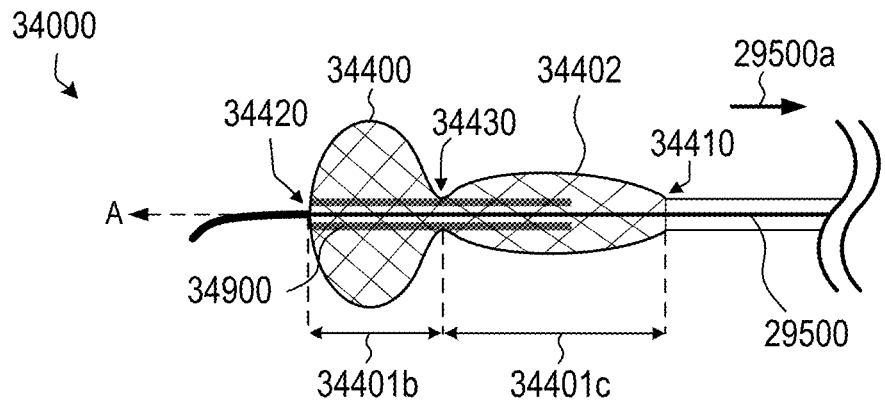
Figure 34C:
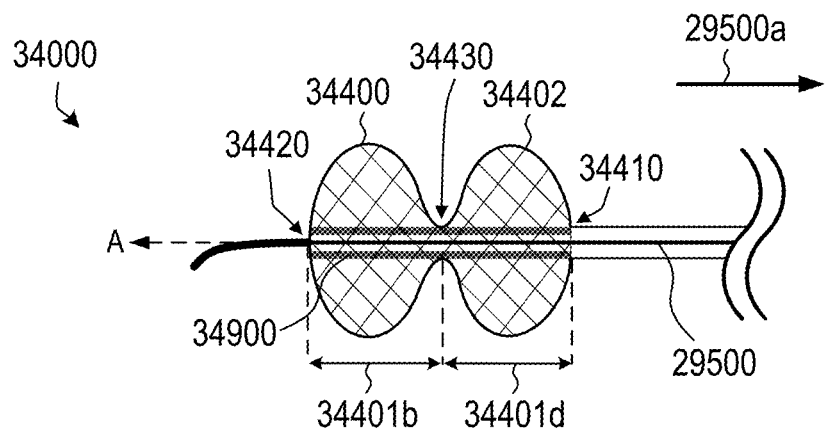

FIGS. 34A-C illustrate another exemplary intraluminal device 34000 having multiple radially-expandable mesh segments 34400, 34402 and a single expansion limiter 34900 configured to limit expansion of both mesh segments. In some embodiments, expansion limiter 34900 may be secured to the interior surface of transition zone 34430 by solder, welding, adhesive, one or more mechanical fasteners, or other suitable means. Although expansion limiter 34900 is configured as a cylindrical tube in the example of FIGS. 34A-C, expansion limiter 34900 may alternatively be configured as a helical coil or may have any other suitable configuration. Core wire 29500 may extend through both mesh segments 34400 and 34402 and through expansion limiter 34900, and may be secured to a portion of the distal mesh segment 31400 (e.g., to mesh segment distal end 31420).

Axial movement of core wire 29500 (e.g., under control of wire actuator 29112) may control expansion and contraction of both mesh segments 34400 and 34402 between their respective radially-contracted and radially-expanded states. As illustrated in FIGS. 34A-C, mesh segments 34400 and 34402 may be expanded sequentially in at least some embodiments, with the distal-most mesh segment 34400 expanding first and the proximal-most mesh segment 34402 expanding last. In some embodiments, core wire 29500 may pull mesh segment distal end 34420 proximally towards transition zone 34430, causing radial expansion of distal mesh segment 31400 while proximal mesh segment 31402 remains radially contracted. Distal mesh segment 31400 may be fully radially-expanded when the distal end of the distal mesh segment contacts the expansion limiter 34430; this configuration is illustrated in FIG. 34B. At this point, additional proximally-directed force from the core wire 29500 is transmitted to transition zone 34430 via its attachment to expansion limiter 34900. The applied force may pull transition zone 34430 proximally towards the mesh segment proximal end 34410, causing radial expansion of the proximal mesh segment 34402 until the expansion limiter 34430 is pulled into contact with the proximal end of the proximal mesh segment 34402. At this point, exemplary intraluminal device 34000 may be configured in the state illustrated in FIG. 34C; any additional proximally-directed force may be prevented from causing further expansion (and thus foldback) of the mesh segments 34400 and 34402 due to the engagement of the expansion limiter 34900 with the proximal end 34420 and distal end 34410 of the mesh segments. Advantageously, utilizing a single expansion limiter 34900 to control multiple mesh segments may reduce the number of components within intraluminal device 34000 and may require fewer assembly steps.

Figure 35A:
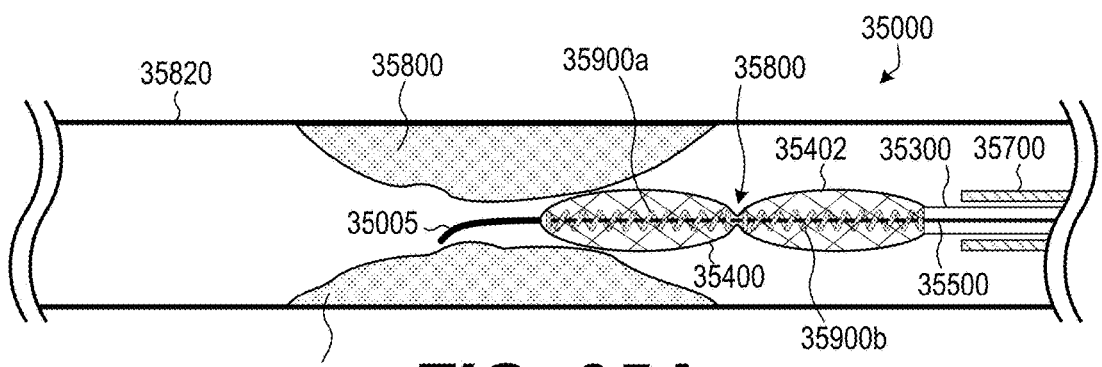
FIGS. 35A-C illustrate a method of removing occlusive material from a body lumen with an exemplary intraluminal device, in accordance with at least one of the disclosed embodiments.
Figure 35B:
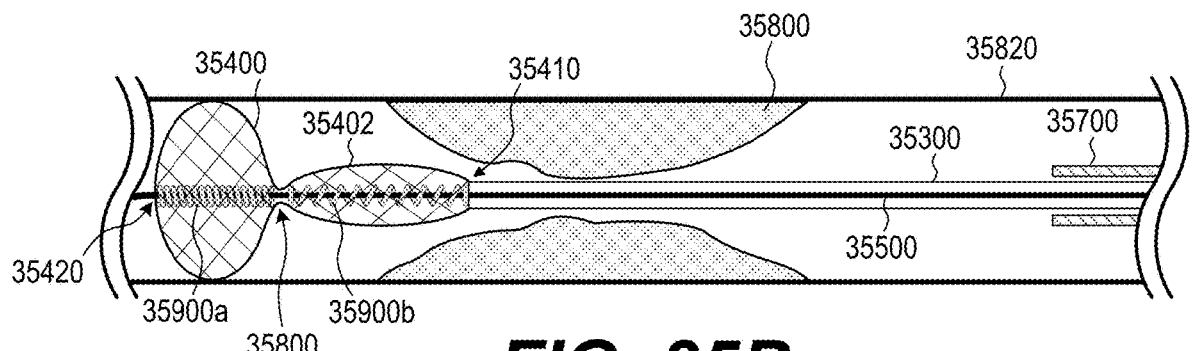
Figure 35C:
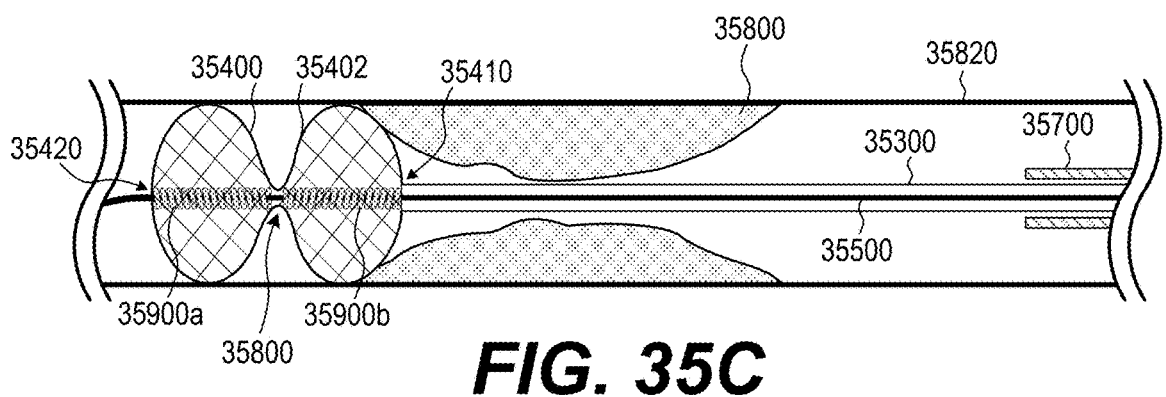

FIGS. 35A-C illustrate a method of removing occlusive material 35800 from a body lumen 35820 with an exemplary intraluminal device 35000. In FIG. 35A, the intraluminal device 35000 may be delivered into the lumen 35820 via a delivery catheter 35700. Intraluminal device 35000 may include at least one expandable mesh segment at the distal end of shaft portion 35300. Although the example depicted in FIGS. 35A-C depicts an intraluminal device 35000 with two expandable mesh segments 35400 and 35402, any suitable number of mesh segments may be utilized with intraluminal device 35000, such as one mesh segment, two mesh segments, three mesh segments, four mesh segments, or some other number of mesh segments. Mesh segments 35400 an 35402 may include expansion limiters 35900a and 35900b, respectively. Although the example depicted in FIGS. 35A-C depicts expansion limiters 35900a and 35900b configured as helical coils, any suitable configuration of expansion limiters may be utilized with intraluminal device 35000, such as a cylindrical shaft.

In FIG. 35A, intraluminal device 35000 may be delivered to an upstream side of occlusive material 35800, with mesh segments 35400 and 35402 in their respective radially-contracted states. As shown in FIG. 35B, at least one of the mesh segments 35400 and 35402 may be delivered downstream of occlusive material 35800. In some embodiments, the occlusive material 35800 may be positioned proximal to proximal-most mesh segment (i.e., proximal mesh segment 35402). Additionally, or alternatively, the occlusive material 35800 may be positioned between two consecutive mesh segments. Core wire 35500 may then be pulled proximally (i.e., to the right in FIG. 35B), causing radial expansion of distal mesh segment 35400, while proximal mesh segment 35402 may remain radially-contracted. Radial expansion of distal mesh segment 35400 may continue until further expansion is prevented by expansion limiter 35900a. As illustrated in FIG. 35C, additional actuation of core wire 35500 may cause radial expansion of proximal mesh segment 35402 until further expansion is prevented by expansion limiter 35900b. After both mesh segments 35400 and 35402 are fully radially-expanded, further radial expansion of the mesh segments may be prevented by expansion limiters 35900a and 35900b.

Once the mesh segments 35400 and 35402 are fully expanded, as depicted in FIG. 35C, the mesh segments may form a filter configured to trap portions of the occlusive material 35800. The intraluminal device 35000 may be pulled proximally until at least the proximal-most mesh segment (i.e., proximal mesh segment 35402) comes in contact with the occlusive material 35800. Continued proximal movement of intraluminal device 35000 causes the mesh segments 35400 and 35402 to push the occlusive material 35800 proximally and into catheter 35700. In some embodiments, at least one of the mesh segments 35400 and 35402 may remain radially-expanded until the occlusive material 35800 is captured and removed from the body lumen 35820.

Figure 36A:
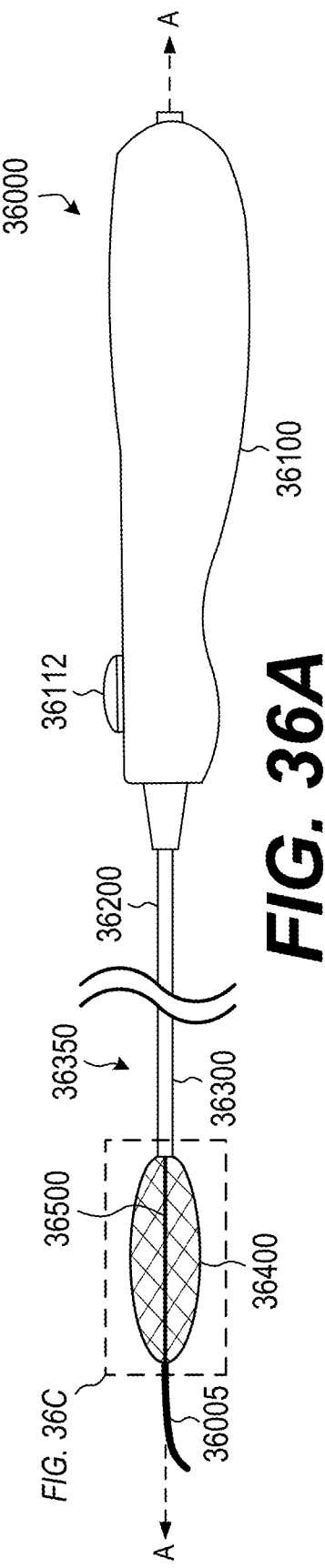
FIGS. 36A and 36B illustrate another exemplary intraluminal device, in accordance with at least one of the disclosed embodiments.
Figure 36B:
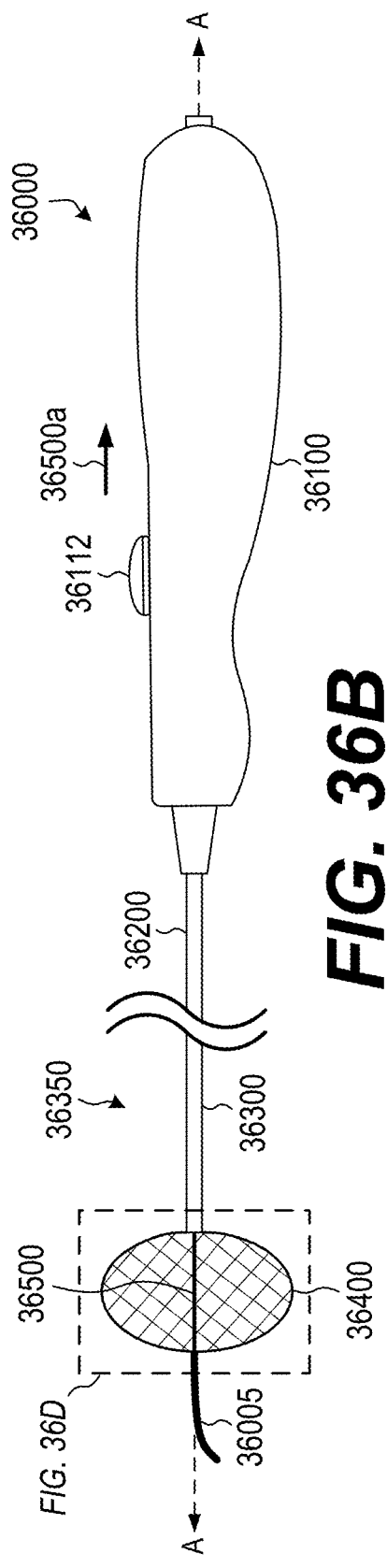

FIGS. 36A and 36B illustrate an exemplary intraluminal device 36000. Intraluminal device 36000 may include a control handle 36100, a proximal shaft portion 36200 extending from the distal end of the control handle 36100, and a distal shaft portion 36300 extending from, or otherwise connected to, the distal end of proximal shaft portion 36200. Proximal shaft portion 36200 and distal shaft portion 36300 may form a hollow, elongated shaft 36350 of intraluminal device 36000 extending along a longitudinal axis A of the intraluminal device. A flexible, atraumatic tip 36005 may optionally be secured to the distal end of the intraluminal device 36000. Intraluminal device 36200 may include an expandable mesh segment 36400 connected to, or otherwise secured relative to, the distal end of the elongated shaft 36350. Mesh segment 36400 may be configured for radial expansion and contraction between a radially-contracted state (e.g., the state illustrated in FIGS. 36A and 36C) and a radially-expanded state (e.g., the state illustrated in FIGS. 36B and 36D). Intraluminal device 36000 may also include a core wire 36500, which may be connected to a portion of the expandable mesh segment 36400 (e.g., the distal end of mesh segment 36400) and may extend through the elongated shaft 36350 to the control handle 36100. Core wire 36500 may be secured to a wire actuator 36112 in the control handle 36100, which may be configured to effect axial movement of the core wire 36500 to control expansion and contraction of the mesh segment 36400.

In some embodiments, elongated shaft 36350 and core wire 36500 may be secured to different portions of expandable mesh segment 36400. In some embodiments, elongated shaft 36350 may be secured to the proximal end 36410 of the mesh segment, and core wire 36500 may be secured to the distal end 36420 of the mesh segment. In addition, elongated shaft 36350 and core wire 36500 may both be configured for axial movement relative to control handle 36100 (via a mechanism detailed below). Accordingly, elongated shaft 36350 and core wire 36500 may both be configured to radially expand and contract the mesh segment 36400. For example, elongated shaft 36350 may be configured to expand the mesh segment 36400 by pushing the proximal end 36410 of the mesh segment distally, towards distal end 36420. Core wire 36500 may be configured to expand the mesh segment 36400 by pulling the distal end 36420 of the mesh segment proximally, towards proximal end 36410. Elongated shaft 36350 and core wire 36500 may also be configured to contract the mesh segment 36400 by the opposite movements.

Figure 36D:
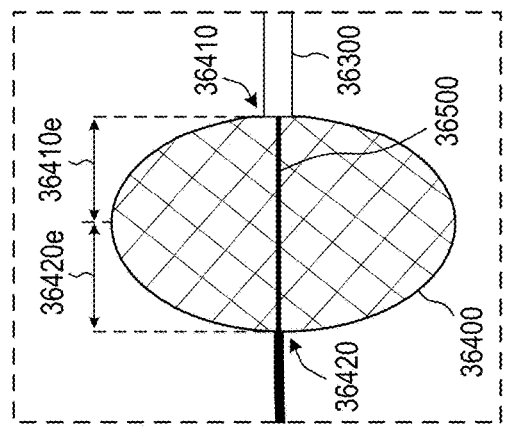
FIGS. 36C and 36D illustrate enlarged views of an expandable mesh segment of the exemplary intraluminal device shown in FIGS. 36A and 36B.
Figure 36C:
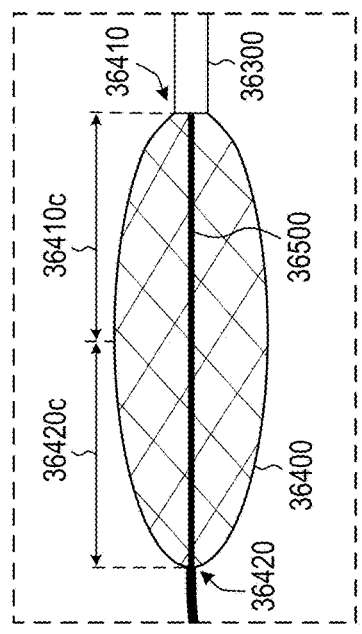

In some embodiments, elongated shaft 36350 and core wire 36500 may be configured to drive expansion of mesh segment 36400 simultaneously, from both the proximal end 36410 of the mesh segment and the distal end 36420 of the mesh segment. For example, FIGS. 36C and 36D show enlarged views of the contracted and expanded mesh segment 36400, respectively. During transition from the radially-contracted state shown in FIG. 36C to the radially-expanded state shown in FIG. 36D, core wire 36500 may pull distal end 36420 in a proximal direction at the same time that elongated shaft 36350 pushes proximal end 36410 in a distal direction. In some embodiments, the proximal end 36410 and distal end 36420 of the mesh segment 36400 may be configured to move the same axial distance during radial expansion of the mesh segment. For example, in FIG. 36C, 36410c and 36420c represent an axial length between the midpoint of the mesh segment 36400 and the distal end 36410 and proximal end 36420 of the mesh segment, respectively, when the mesh segment is in the radially-contracted state. Similarly, in FIG. 36D, 36410e and 36420e represent an axial length between the midpoint of the mesh segment 36400 and the distal end 36410 and proximal end 36420 of the mesh segment, respectively, when the mesh segment is in the radially-expanded state. The proximal end 36410 and distal end 36420 may be moved the same axial distance by the elongated shaft 36300 and core wire 36500, respectively, during expansion and contraction of the mesh segment 36400. As a result, the difference between distances 36410c and 36410e may be equal to the difference between distances 36420c and 36420e. As a result, the midpoint of the mesh segment 36400 may remain stationary during expansion and contraction, leading to improved anchoring and easier monitoring of the mesh location.

Figure 36F:
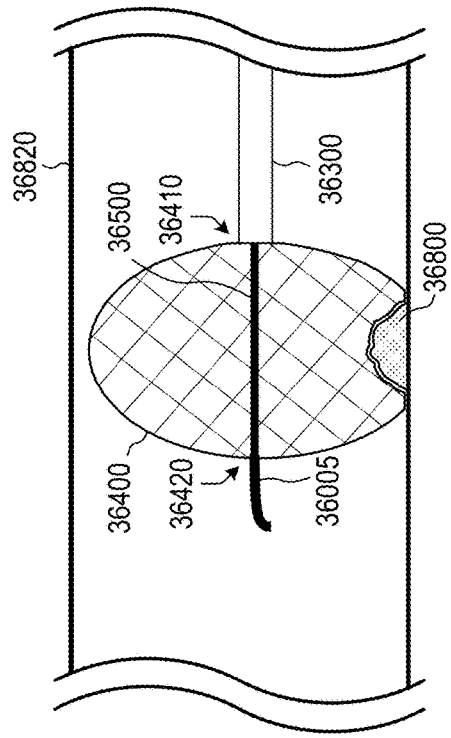
FIGS. 36E and 36F illustrate radial-expansion of the mesh segment shown in FIGS. 36C and 36D within a body lumen.
Figure 36E:
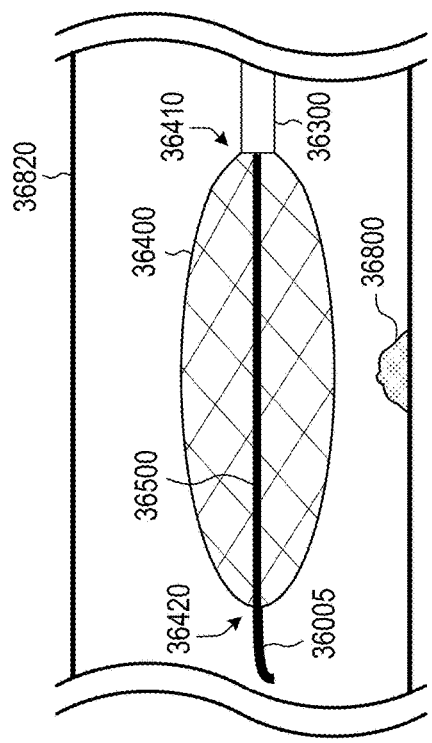

Advantageously, expanding the mesh segment 36400 from both ends may allow more uniform expansion of the mesh segment, especially in environments in which a portion of the mesh segment 36400 encounters resistance (such as from a clot or small vessel). For example, FIGS. 36E and 36F illustrate radial-expansion of the mesh segment 36400 within a body lumen 36820 having occlusive material 36800. Because mesh segment 36400 is expanded from both the distal end 36420 and proximal end 36410, it may engage the occlusive material 36800 from both the distal and proximal directions. For example, if the occlusive material 36800 creates resistance against the axial movement of the core wire 36500, thus limiting the ability of the core wire 36500 to radially expand the mesh segment 36400, the elongated shaft 36300 may complete radial expansion of the mesh segment 36400 and ensure that the occlusive material 36800 is fully engaged by the mesh segment (leading to better penetration of the occlusive material 36800). As a result, the mesh segment 36400 may contact a larger surface area of the body lumen 36820 and provide more uniform and larger magnitude force application to the body lumen 36820.

Figure 37A:
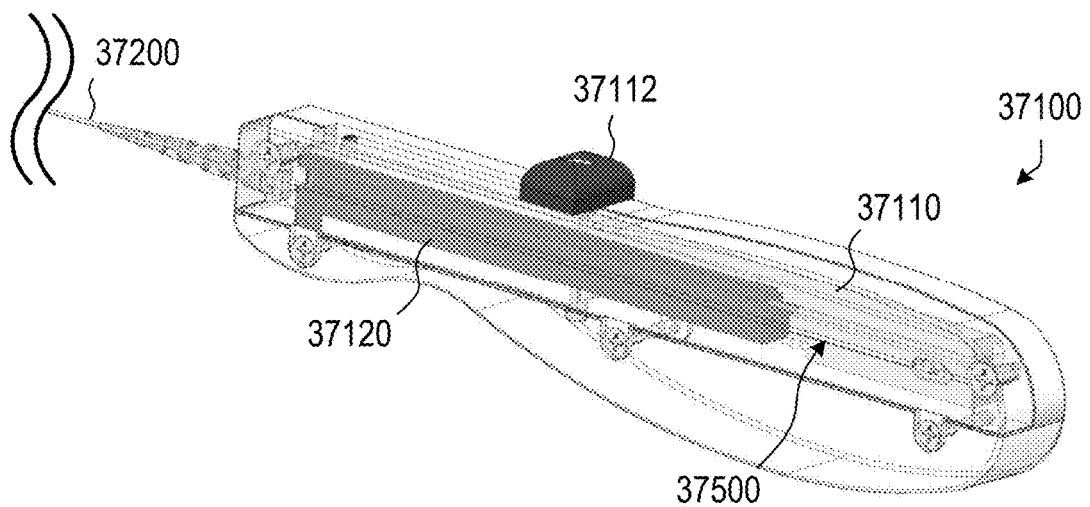
FIGS. 37A-C illustrate a handle of an exemplary intraluminal device, in accordance with at least one of the disclosed embodiments.
Figure 37B:
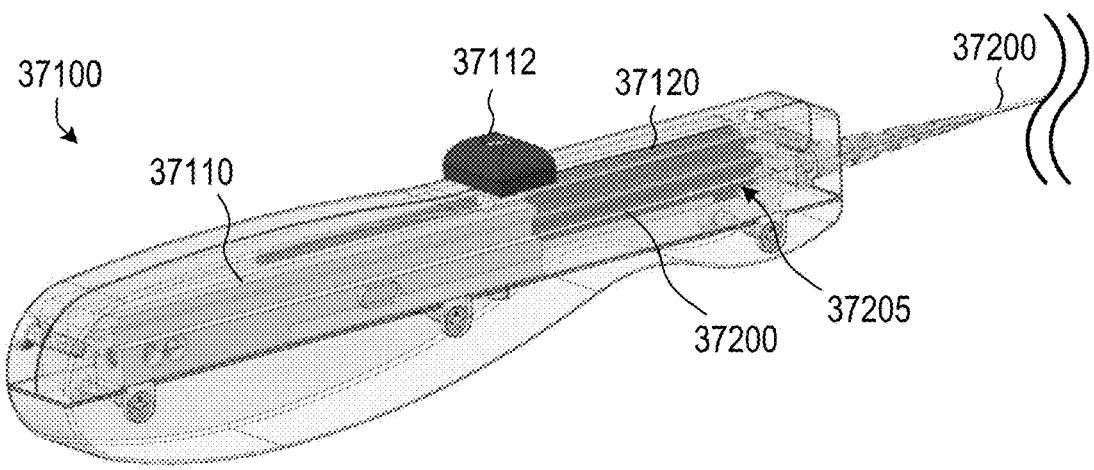
Figure 37C:
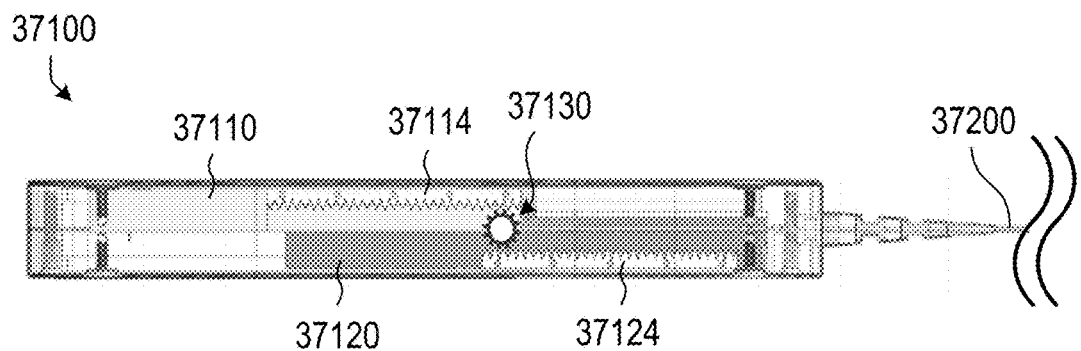

FIGS. 37A-C illustrate an exemplary control handle 37100 of an intraluminal device. Control handle 37100 may be configured to affect simultaneous axial movement of the elongated shaft and the core wire to expand the mesh segment (not pictured in FIGS. 37A-C). Control handle 37100 may include a first handle segment 37110 that is secured relative to the core wire 37500. In some embodiments, core wire 37500 may extend into the control handle 37100 and may be secured to the first handle segment 37110 by solder, welding, adhesive, one or more mechanical fasteners, or other suitable means. Accordingly, axial movement of the first handle segment 37110 may cause corresponding axial movement of the core wire 37500. The first handle segment 37110 may additionally be operably connected to wire actuator 37112, which may include any appropriate mechanism for actuating axial movement of core wire 37500, examples of which include, but are not limited to, a rotatable knob, a wheel, a button, a slider, a lever, a joystick, a touchpad, and combinations thereof. In some embodiments, wire actuator 37112 may affect axial movement of the first handle segment 37110, which may cause corresponding axial movement of the core wire 37500.

Control handle 37100 may additionally include a second handle segment 37120 that is secured relative to the proximal shaft segment 37200, and thus, to the entire elongated shaft of the intraluminal device. In some embodiments, proximal shaft segment 37200 may extend into the control handle 37100 and may be secured to the second handle segment 37120 by solder, welding, adhesive, one or more mechanical fasteners, or other suitable means. For example, in FIG. 37B, site 37205 may be a location of connection between the second handle segment 37120 and the proximal shaft segment 37200. As a result, axial movement of the second handle segment 37120 may cause corresponding axial movement of the proximal shaft segment 37200 and elongated shaft.

FIG. 37C illustrates a bottom plan view of the control handle 37100. As shown in FIG. 37C, the first handle segment 37110 may include a first toothed rack 37114 and the second handle segment 37120 may include a second toothed rack 37124. Both racks may engage a rotating gear 37130, which may be configured to synchronize opposite axial movement of the handle segments 37110, 37120. In some embodiments, when the first handle segment 37110 moves in a first axial direction (e.g., in a distal direction) due to actuation of the wire actuator 37112, first toothed rack 37114 may rotate gear 37130, which may in turn drive axial movement of the second toothed rack 37124, and thus the entire second handle segment 37120, in a second axial direction that is opposite to the first axial direction (e.g., in a proximal direction). As a result, actuation of the wire actuator 37112 may cause opposite axial movements of the core wire 37500 and the elongated shaft, thus controlling radial expansion and contraction of the expandable mesh segment.

In some embodiments, the first handle segment 37110 and second handle segment 37120 may be configured to have a 1:1 movement ratio, such that the segments move the same axial distance in opposite directions. In some alternative embodiments, the first handle segment 37110 and second handle segment 37120 may be configured to have a different movement ratio, such as a 2:1 movement ratio, a 1:2 movement ratio, or any other suitable movement ratio. As a result, axial movement of one handle segment may correspond to an axial movement by the other handle segment that is a fraction of the distance. The movement ratio may be controlled by suitable mechanism, such as by incorporating an additional rotating gear into control handle 37100, such that racks 37114 and 37124 are configured to have a different movement ratio.

In alternative embodiments, other structures may be utilized in place of the elongated shaft and/or the core wire. Other structures may include, for example, any composition of tubes, cable, coils, or other suitable elements.

Figure 38A:
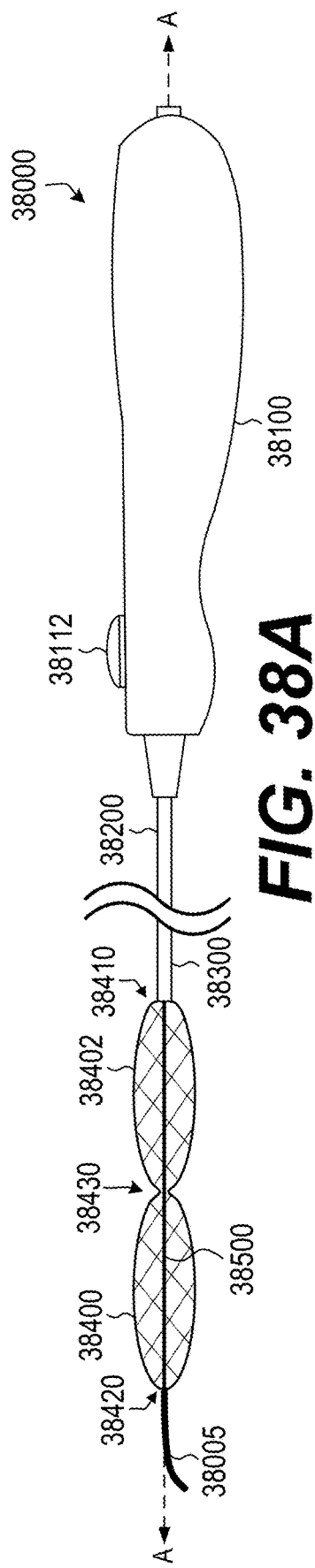
FIGS. 38A and 38B illustrate another exemplary intraluminal device, in accordance with at least one of the disclosed embodiments.
Figure 38B:
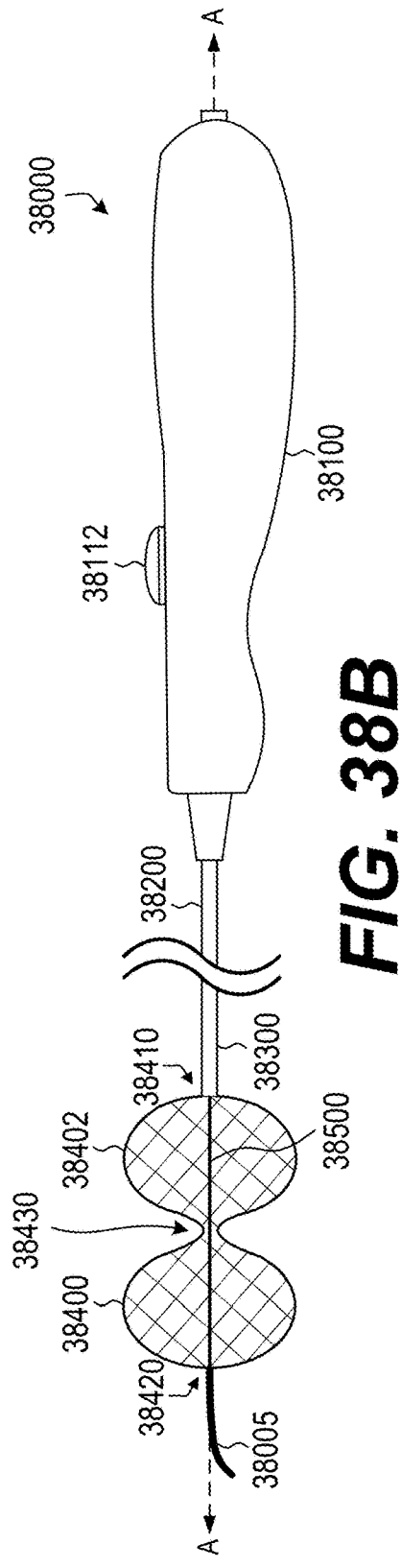

FIGS. 38A and 38B illustrate an exemplary intraluminal device 38000 having multiple mesh segments 38400 and 38402. Although the example illustrated in FIGS. 38A and 38B includes two mesh segments 38400 and 38402, those of ordinary skill will understand that intraluminal device 38000 may include one mesh segment, two mesh segments, three mesh segments, four mesh segments, five mesh segments, or any other suitable number of mesh segments. Intraluminal device 38000 may be configured to actuate synchronized axial movement of the shaft segments 38200, 38300 and of core wire 38500, as discussed above. For example, core wire 38500 may be configured to move mesh segment distal end 38420 in a first axial direction, and the elongated shaft may be configured to move mesh segment proximal end 38410 in a second, opposite axial direction. As a result, the core wire and elongated shaft may drive the radial expansion and contraction of all mesh segments 3840, 38402 simultaneously.

FIGS. 39A and 39B illustrate an exemplary intraluminal device 39000 delivered through a catheter 39700. In some embodiments, the distal end of intraluminal device 39000 may be passed through a first opening 39702 of the catheter and advanced distally to a treatment site within the body. The distal end of the intraluminal device 39000 may emerge from the distal end of the catheter 39700, such that the expandable mesh portion 39400 may engage with the anatomy at the treatment site and may be configured for radial-expansion without being constrained by the catheter 39700. The control handle 39100 of the intraluminal device may include a handle-shaft 39150, which may extend distally from the handle over at least a portion of the elongated shaft (including at least a portion of the proximal shaft segment, which is not depicted in FIGS. 39A and 39B).

Handle-shaft 39150 may be secured against movement relative to the control handle 39100. Once the intraluminal device 39000 advanced through the catheter 39700, the catheter opening 39702 may be removably locked to the handle-shaft 39150, thus securing the catheter 39700 and control handle 39100 together. Once locked to the catheter 39700, the wire actuator 39112 in the control handle 39100 may be actuated to control the synchronized axial movements of the core wire 39500 and the elongated shaft to expand and contract the mesh segment 39400. Advantageously, this locking configuration may improve the maneuverability of the intraluminal device 39000 while the distal end thereof is positioned within the body, and may make it easier for the user to control expansion of the mesh segment 39400.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods can be modified in any manner, including by reordering steps or inserting or deleting steps. It is intended, therefore, that the specification and examples be considered as example only, with a true scope and spirit being indicated by the following claims and their full scope of equivalents.

What is claimed is:

1. A method of removing a clot from a body lumen, the method comprising:

positioning a radially-expandable mesh segment of an intraluminal device downstream of the clot in the body lumen while the mesh segment is in a radially-contracted state, the mesh segment having a proximal end and a distal end, wherein the intraluminal device comprises:

a hollow elongated shaft secured relative to the proximal end of the mesh segment, a core wire affixed to the distal end of the mesh segment, and a handle configured to control axial movement of the elongated shaft and core wire;

radially-expanding the mesh segment downstream of the clot in the body lumen, wherein radially-expanding the mesh segment includes:

manipulating the elongated shaft to move the proximal end of the mesh segment a first distance in a first direction relative to the handle of the intraluminal device, and manipulating the core wire to move the distal end of the mesh segment a second distance in a second direction relative to the handle of the intraluminal device, wherein the first distance is equal to the second distance and wherein the first direction is opposite the second direction;

moving the radially-expanded mesh segment into engagement with the clot; and removing the clot by moving the radially-expanded mesh segment in an upstream direction.

2. The method of claim 1, wherein the handle of the intraluminal device simultaneously actuates the elongated shaft and the core wire to move the proximal and distal ends of the mesh segment, respectively, during radial expansion of the mesh segment.

3. The method of claim 1, wherein the first direction is a distal direction and the second direction is a proximal direction.

4. The method of claim 1, wherein the elongated shaft is situated proximal to the mesh segment, wherein the handle is situated proximal to the elongated shaft, and wherein the elongated shaft and the core wire move axially relative to the handle during radial expansion of the mesh segment.

5. The method of claim 1, wherein the elongated shaft and the core wire move simultaneously relative to the handle of the intraluminal device to radially expand the mesh segment.

6. The method of claim 1, wherein radially-expanding the mesh segment comprises:

axially moving the proximal end of the mesh segment relative to the distal end of the mesh segment with the elongated shaft; and axially moving the distal end of the mesh segment relative to the proximal end of the mesh segment with the core wire.

7. The method of claim 1, wherein the handle comprises:

a first handle segment secured relative to the core wire; and a second handle segment secured relative to the elongated shaft, wherein the first handle segment and second handle segment move the same distance in opposite axial directions during radial expansion of the mesh segment.

8. The method of claim 1, wherein radially-expanding the mesh segment includes simultaneously moving a distal end of the elongated shaft the first distance in the first direction and moving a distal end of the core wire the second distance in the second direction.

* * * * *